US006720307B2

(12) United States Patent
Tuinman et al.

(10) Patent No.: US 6,720,307 B2
(45) Date of Patent: *Apr. 13, 2004

(54) GLYCOSYLATED ANALOGS OF FUSIDIC ACID

(75) Inventors: Roeland Tuinman, Northville, MI (US); Masato Koreeda, Ann Arbor, MI (US); Brian Keith Shull, Durham, NC (US)

(73) Assignee: The University of Michigan, Ann Arbor, MI (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/189,242

(22) Filed: Jul. 2, 2002

(65) Prior Publication Data

US 2003/0004321 A1 Jan. 2, 2003

Related U.S. Application Data

(63) Continuation of application No. 09/616,658, filed on Jul. 14, 2000, now Pat. No. 6,462,182, which is a continuation of application No. 08/623,335, filed on Mar. 27, 1996, now Pat. No. 6,103,884.

(51) Int. Cl.$^7$ .......................... A61K 31/70; A61K 31/56
(52) U.S. Cl. .......................... 514/26; 514/169; 514/182; 536/5; 552/504
(58) Field of Search .......................... 514/26, 182, 169; 536/5; 552/504

(56) References Cited

U.S. PATENT DOCUMENTS

| 4,004,004 A | * | 1/1977 | von Daehne | 514/182 |
|---|---|---|---|---|
| 4,410,515 A | | 10/1983 | Holick et al. | 424/180 |
| 5,278,296 A | | 1/1994 | Klemke | 536/5 |

FOREIGN PATENT DOCUMENTS

EP          0300073      1/1989

OTHER PUBLICATIONS

Brown and Thomas, "O–Glycosidation: Application to the Synthesis of Drug Molecules," *Aust. J. Pharm. Sci.* 8: 1–10 (1979).
Coombs, "Fusidic acid in staphylococcal bone and joint infection," *J. Antimicrob. Chemotherapy* 25: Supp. B: 53–60 (1990).
Ferrier, "Unsaturated Carbohydrates. Part IX. Synthesis of 2,3–Dideoxy–α,D–erythro–hex–2–enopyranosides from Tri–O–acetyl–D–glucal," *J. Chem. Soc.* C, pp. 570–575 (1969).
Ferrier, "1038. Unsaturated Carbohydrates. Part II. Three Reactions Leading to Unsaturated Glycopyranosides," *J. Chem. Soc.*, pp. 5443–5449 (1964).
Ferrier et al., "712. The Reaction Between 3,4,6–Tri–O–acetyl–D–glucal and nitrophenol," *J. Chem. Soc.*, pp. 3667–3670 (1962).

Godtfresden et al., "Fucidin, A New Orally Active Antibiotic," *Lancet* 1: 928–931 (1962).
Godtfresden et al., "Fusidic Acid Derivatives. I. Relationship between Structure and Antibacterial Activity," *J. Med. Chem.* 9: 15–22 (1966).
Goodman and Gilman, "The Pharmacological Basis of Therapeutics, Ninth Edition" p. 1683, The Mc–Graw–Hill Companies (1996).
Helferich, "The Glycals," *Adv. Carbohydrate Chem.* 7: 209–245 (1952).
Hording et al., "Fusidic Acid Treatment of HIV Infection: No Significant Effect in a Pilot Trial," *Scand.J. Infect. Disease* 22: 649–652 (1990).
Jensen et al., "Clinical experiences with fusidic acid in cystic fibrosis patients," *J. Antimicrob. Chemotherapy* 25: Supp. B:45–52 (1990).
Ji et al., "Monophosphoric Acid Diesters of 7β–Hydroxycholesterol and of Pyrimidine Nucleosides as Potential Antitumor Agents: Synthesis and Preliminary Evaluation of Antitumor Activity," *J. Med. Chem.* 33: 2264–2270 (1990).
Kleeman et al., "Renin Inhibitory Pentols Showing Improved Enteral Bioavailability," *J. Med. Chem.* 35: 559–567 (1992).
Mathew et al., "Synthesis and Evaluation of Some Water–Soluble Prodrugs and Derivatives of Taxol with Antitumor Activity," *J. Med. Chem.* 35: 145–151 (1992).
Tanaka et al., "Mechanism of Protein Synthesis Inhibition By Fusidic Acid and Related Antibiotics," *Biochem. & Biophys. Res. Commun.* 30: 278–283 (1968).
Verbist, "The antimicrobial activity of fusidic acid," *J. Antimicrob. Chemotherapy* 25: Supp. B:1–5 (1990).
Youle et al., "Clinical, Immunological, and Virological Effects of Sodium Fusidate in Patients with AIDS or AIDS–Related Complex (ARC): An Open Study," *J. Acquired Immune Deficiency Syndrome* 2: 59–62 (1989).
Schmidt, "New Methods for the Synthesis of Glycosides and Oligosaccharides—Are There Alternatives to the Koenigs–Knorr Method?" *Angew. Chem. Int. Ed. Eng.* 25: 212–235 (1986).
Toshima and Tatsuta, "Recent Progress in O–Glycosylation Methods and Its Application to Natural Products Synthesis," *Chem. Rev.* 93: 1503–1531 (1993).

(List continued on next page.)

*Primary Examiner*—Elli Peselev
(74) *Attorney, Agent, or Firm*—Medlen & Carroll LLP

(57) ABSTRACT

Novel analogs of fusidic acid are described with one or more carbohydrate units attached. Certain glycosylated analogs of fusidic acid have enhanced solubility properties in diluents or excipient of choice as compared to unmodified fusidic acid. Certain glycosylated analogs may be employed as chemotherapeutic agents and particular analogs may be useful for fighting anti-microbial infections.

23 Claims, 30 Drawing Sheets

OTHER PUBLICATIONS

Kochetkov, "Recent Developments in the Synthesis of Polysaccharides and Stereospecificity of Glycosylation Reactions," *Studies in Natural Products Chemistry*, vol. 14, Atta–ur–Rahman (ed.), pp. 201–266, Elsevier Science B.V (1994).

Hacksell and Daves, Jr., "Stereocontrolled Palladium (II)–Mediated Coupling of Furanoid Glycals with a Pyrimidinylmercuric Salt. Facile C–Nucleoside Syntheses," *J. Org. Chem.* 48: 2870–2876 (1983).

Tanabe, "Partial Synthesis of Fusidic Acid," *Tetrahedron Lett.* 17: 1481–1484 (1977).

Janssen and Vanderhaeghe, "Modification of the Side Chain of Fusidic Acid (Ramycin)," *J. Med. Chem.* 10: 205–208 (1967).

Godtfredsen and Vangedal, "The Structure of Fusidic Acid," *Tetrahedron* 18: 1029–1048 (1962).

Godtfredsen et al., "The Stereochemistry of Fusidic Acid," *Tetrahedron* 21: 3505–3530 (1965).

Riisom et al., "Assignment of the $^{13}$C NMR Spectra of Fusidic Acid Derivatives. Biosynthetic Incorporation of Sodium [1–$^{13}$C]–Acetate into Fusidic Acid," *Tetrahedron Lett.* 26: 2247–2250 (1974).

Tanaka, "Fusidic Acid," *Antibiotics* 3: 436–447 (1975).

Barber and Waterworth, "Antibacterial Activity In Vitro Of Fusidin," *Lancet*, pp. 931–932 (1962).

Hilson, "In–Vitro Studies of a New Antibiotic (Fucidin)," *Lancet*, pp. 932–933 (1962).

Taylor and Bloor, "Antistaphylococcal Activity of Fucidin," *Lancet*, pp. 935–937 (1962).

Rowe et al., "An experimental evaluation of the pharmacokinetics of fusidic and in peritoneal dialysis," *J. Med. Microbiol.* 36: 71–77 (1992).

Petersen and Thomsen, "Fusidic acid cream in the treatment of plasma cell balanitis," *J. Am. Acad. Dermatology* 27: 633–634 (1992).

Torres and Raoult, "In Vitro Activities of Ceftriaxone and Fusidic Acid against 13 Isolates of *Coxiella burnetti*, Determined Using the Shell Vial Assay," *Antimicrobial Agents and Chemotherapy* 37: 491–494 (1993).

Bendtzen et al., "Fusidic Acid, an Immunosuppressive Drug with Functions Similar to Cyclosporin A," *Cytokine* 2: 423–429 (1990).

Markowitz et al., "In Vitro Susceptibility Patterns of Methicillin–Resistant and –Susceptible *Staphylococcus aureus* Strains in a Population of Parenteral Drug Abusers from 1972 to 1981," *Antimicrobial Agents and Chemotherapy* 23: 450–457 (1983).

Huebner et al., "In vitro Susceptibility of Methicillin–Resistant *Staphylococcus aureus* and Slime–Producing and Non–Slime–Producing Coagulase–Negative Staphylococci to Fusidic Acid," *Chemotherapy* 38: 206–210 (1992).

Peter et al., "Pharmacokinetics of Intravenous Fusidic Acid in Patients with Cholestasis," *Antimicrobial Agents and Chemotherapy* 37: 501–506 (1993).

Barnes, "On the Shelf AIDS Drug in Clinical Trial," *Science* 238: 276 (1987).

Hoel et al., "In vitro antimicrobial susceptibility testing of rapidly growing mycobacteria using the tablet diffusion method: resistance pattern of Norwegian *Mycobacterium fortuitum* and *Mycobacterium chelonae* isolates," *APMIS* 101: 27–32 (1993).

Scowen and Garrod, "A Case of Staphylococcal Septicaemia Treated With Penicillin and Fucidin," *Lancet*, pp. 933–935 (1962).

Iwasaki et al., "Revised Structure of Helvolic Acid," *Chem. Commun.*, pp. 1119–1120 (1970).

Teknetzis et al., "Acanthosis nigricans–like lesions after local application of fusidic acid," *J. Am. Acad. Dermatology* 28: 501–502 (1993).

Dess and Martin, "Readily Accessible 12–I–5 Oxidant for the Conversion of Primary and Secondary Alcohols to Aldehydes and Ketones," *J. Org. Chem.* 48: 4155–4156 (1983).

Danishefsky et al., "A Strategy for the Solid–Phase Synthesis of Oligosaccharides," *Science* 260: 1307–1309 (1993).

Windholz et al. (eds.), *The Merck Index*, 9th ed., Merck & Co., Inc., Rahway, NJ, (1976) fusidic acid entry only.

* cited by examiner

GLYCOSYLATED ANALOGS OF FUSIDIC ACID

This application is a continuation of application Ser. No. 09/616,658 filed 07/14/2000, now U.S. Pat. No. 6,462,182, which is a continuation of application Ser. No. 08/623,335 filed Mar. 27, 1996, now U.S. Pat. No. 6,103,884.

FIELD OF THE INVENTION

The present invention relates to novel analogs of fusidic acid. In particular, the present invention relates to novel glycosylated analogs of fusidic acid. The present invention also relates to novel glycosylated analogs of fusidic acid that have different solubility properties than unmodified fusidic acid and that act as chemotherapeutic agents.

BACKGROUND OF THE INVENTION

The discovery of antibiotics was possibly the most important medical breakthrough of the twentieth century, making many previously lethal microbial infections easily treatable. However, the benefits of antibiotic therapy have gradually given rise to a dangerous development, namely antibiotic-resistant microorganisms. Through the constant use, and often overuse, of antibiotics, mankind has begun the process of selecting strains of bacteria which are resistant to many types of antibiotics.

Physicians employ many strategies to deal with antibiotic resistance, including: aggressively searching for new antibiotics, prescribing existing antibiotics in a more prudent and less frequent manner, and using combinations of diverse antibiotics to treat infections. In order to successfully employ the latter strategy, it is necessary to utilize a combination of antibiotics that have very different biochemical modes of action.

Fusidic acid is just such an antibiotic. Having a mode of action different than most antibiotics, fusidic acid is unlikely to have cross-resistance with other antibiotics against microorganisms.

A relatively new antibiotic, fusidic acid was discovered in 1962 by Godtfresden and coworkers [See Godtfresden et al., Lancet 1:928 (1962); and, Verbist, J. Antimicrob. Chemotherapy 25: Supp. B:1 (1990)]. It was isolated from the fermentation broth of the fungus *Fusidium coccineum*. It is a steroid-like antibiotic belonging to the class of the fusidanes, chemically related to cephalosporin $P_1$ and to helvolic acid. Of these fusidanes, however, only fusidic acid has been used clinically with success.

Fusidic acid is most effective against Gram-positive bacteria. In particular, *Staphylococcus aureus*, *S. epidermidis*, Clostridium spp. and corynebacteria are highly susceptible [See Verbist supra]. In addition, a few Gram-negative bacteria are susceptible, including Neisseria and Bacteroides spp. However, most Gram negative organisms, including Gram-negative bacilli and fungi, all enterobacteria, Psuedomonas spp., and other non-fermenters are resistant to treatment with fusidic acid. Fusidic acid exhibits moderate efficacy against streptococci, mycobacteria, and Nocardia spp.

Unquestionably, what gives fusidic acid its inherent usefulness in the treatment of microorganisms resistant to other antibiotics is its unique mode of action. Fusidic acid inhibits bacterial protein synthesis by interference with the elongation factor G [See Tanaka et al., Biochem. & Biophys. Res. Commun. 30:278 (1968)]. Such a unique mode of action explains the absence of intrinsic cross-resistance between fusidic acid and any other antibiotics. For example, methicillin-resistant staphylococci are usually susceptible to fusidic acid.

In addition to its usefulness against Gram-positive organisms and bacterial resistance to other antibiotics, there have been recent discoveries related to the use of fusidic acid, which may provide even more clinical benefits.

The use of fusidic acid in treating staphylococcal bone and joint infections has been described [See Coombs, J. Antimicrob. Chemotherapy 25: Supp. B:53 (1990)]. The usefulness of fusidic acid in the treatment of acute osteomyelitis, septic arthritis, chronic osteomyelitis, and other infections encountered in orthopedic surgery merits continued research into the use of fusidic acid for other orthopedic maladies.

Fusidic acid has also recently been shown to be highly effective in treating recurrent bronchopulmonary infections with *Staphylococcus aureus* suffered by patients having cystic fibrosis [See Jensen et al, J. Antimicrob. Chemotherapy 25: Supp. B:45 (1990)].

Perhaps the most exciting recent discovery is the possible use of fusidic acid in the treatment of AIDS. As described by Barnes in a *Science* review [238:276 (1994)], fusidic acid was found by researchers in Denmark to have in vitro effectiveness against HIV as well as "striking clinical improvement" in a 58-year-old Danish man stricken with AIDS. These discoveries have led to immediate efforts to determine whether or not fusidic acid will be useful in the treatment of AIDS. So far, the clinical data have been mixed [See Youle et al, J. Acquired Immune Deficiency Syndromes 2:59 (1989); and, Hording et al, Scand. J. Infect. Disease 22:649 (1990)].

With numerous current uses as well as promising future applications, fusidic acid will remain an important pharmaceutical product for the foreseeable future. However, fusidic acid is practically insoluble in water, and the method of choice for oral delivery of the drug is a film coated formulation of sodium fusidate (the sodium salt) or diethanolamine fusidate (the diethanolamine salt). Both derivatives possess significant side-effects including rashes, gastrointestinal upset, jaundice and other changes in liver function, venospasm, thrombophlebitis, and hemolysis. Clearly, there remains a need for different means of formulation which allows for administration of the agent without inducing serious side-effects.

SUMMARY OF THE INVENTION

The present invention relates to novel analogs of fusidic acid. In particular, the present invention relates to novel glycosylated analogs of fusidic acid. The present invention also relates to novel glycosylated analogs of fusidic acid that have different solubility properties than unmodified fusidic acid and that act as chemotherapeutic agents.

A fusidic acid "derivative" or "analog" of the present invention has the fundamental structure of fusidic acid (see FIG. 1), namely a fused four-ring molecule possessing a steroid-like structure and an alkyl/alkenyl side chain, with either one or more carbohydrate groups attached. The analogs of the present invention have numerous uses. First, they may be successfully employed as standards for analytical techniques (e.g., HPLC) so that new derivatives can be easily identified. Second, the present invention contemplates in vivo use; in accordance with the present invention, a member from the class of novel fusidic acid derivatives is to be delivered as a chemotherapeutic agent, and, in one possible application, to fight anti-microbial infections in the body.

The present invention contemplates derivatives of fusidic acid that have different solubility properties than fusidic acid. These different solubility properties are important because the glycosylated analogs of fusidic acid can be delivered for in vivo use in an admixture with diluent or excipient. It is not intended that the present invention be limited by the nature of the mixture. In one embodiment, the diluent or excipient is propylene glycol. Propylene glycol is miscible in water and a number of organic solvents. Propylene glycol is often used as a substitute for ethylene glycol or glycerol. It can be used as a solvent for oral and injectable drugs and is employed in ointments. [See Goodman and Gilman, The Pharmacological Basis of Therapeutics 9477; and, U.S.P. N.F. 1247]. Dextrose dissolved in an aqueous solution is another diluent or excipient contemplated for this purpose. The aqueous solution used with dextrose can be a buffer or other aqueous solution. For the different diluents or excipient, water or aqueous solutions can be used to dilute the diluent or excipient.

In one embodiment, the present invention contemplates a fusidic acid derivative modified at the C-3 position by chemical, enzymatic, or biological means, such that it contains a carbohydrate unit (See, e.g., FIGS. 2, 3, 10, and 11). In another embodiment, the present invention contemplates a fusidic acid derivative modified at the C-24 and C-25 positions by chemical, enzymatic, or biological means, such that the double bonds present at those positions in unmodified fusidic acid are both reduced to single bonds. The later modifications can be in combination with other modifications, such as those outlined in the first embodiment. In another embodiment, the present invention contemplates a glycosylated analog of fusidic acid modified by chemical, enzymatic, or biological means such that (i) the double bonds at the C-2 and C-3 positions of the saccharide unit bound directly to fusidic acid are both reduced to single bonds, and (ii) the double bonds at the C-24 and C-25 positions of the aglycon are both reduced to single bonds.

In another embodiment, the present invention contemplates a fusidic acid derivative modified at the C-24 position by chemical, enzymatic, or biological means, such that it has a hydroxyl group. In another embodiment, the present invention contemplates a fusidic acid derivative modified at the C-24 position by chemical, enzymatic, or biological means so that the hydroxyl group introduced at the C-24 position has a carbohydrate unit. In another embodiment, the present invention contemplates a fusidic acid derivative modified at the C-24 and C-3 positions by chemical, enzymatic, or biological means such that both positions contain carbohydrate units.

In another embodiment, the present invention contemplates a fusidic acid derivative modified at the C-25 position by chemical, enzymatic, or biological means, such that it has a hydroxyl group. In another embodiment, the present invention contemplates a fusidic acid derivative modified at the C-25 position by chemical, enzymatic, or biological means so that the hydroxyl group introduced at the C-25 position has a carbohydrate unit. In another embodiment, the present invention contemplates a fusidic acid derivative modified at the C-25 and C-3 positions by chemical, enzymatic, or biological means such that both positions contain carbohydrate units.

In another embodiment, the present invention contemplates a fusidic acid derivative modified at the C-11 position by chemical, enzymatic, or biological means, such that it contains a carbonyl group as opposed to the hydroxyl group present at that position in unmodified fusidic acid. In another embodiment, the present invention contemplates a fusidic acid derivative modified by chemical, enzymatic, or biological means, such that it contains one or more carbohydrate units having terminal hydroxyl groups which have been deprotected as opposed to having terminal hydroxyl groups which are protected. In yet another embodiment, the present invention contemplates a fusidic acid derivative modified by chemical, enzymatic, or biological means, such that the C-2 and C-3 positions of any saccharide units bound directly to a hydroxyl group of the aglycon are both reduced to single bonds.

For all these embodiments, the present invention contemplates having glycosylated analogs of fusidic acid or glycosylated analogs of modified forms of fusidic acid with either an α- or β-linkage between the oxygen atom of the hydroxyl group of the aglycon and the C-1 position of the saccharide unit bound to fusidic acid. These two types of analogs are known as the α-anomer and the β-anomer of the glycosylated analog.

The contemplated derivations may be prepared in a number of different fashions, and the present invention contemplates many different possible combinations of these derivations giving rise to different fusidic acid analogs.

The carbohydrate unit or units attached to fusidic acid in some of the aforementioned embodiments are exemplified but not limited to 2,3-desoxy-2,3-dehydroglucose, 2,3-desoxy-2,3-dehydroglucose diacetate, glucoside, glucoside tetraacetate, mannoside, mannoside tetraacetate, galactoside, galactoside tetraacetate, alloside, alloside tetraacetate, guloside, guloside tetraacetate, idoside, idoside tetraacetate, taloside, taloside tetraacetate, rhamnoside, rhamnoside triacetate, maltoside, maltoside heptaacetate, 2,3-desoxy-2,3-dehydromaltoside, 2,3-desoxy-2,3-dehydromaltoside pentaacetate, 2,3-desoxymaltoside, lactoside, lactoside tetraacetate, 2,3-desoxy-2,3-dehydrolactoside, 2,3-desoxy-2,3-dehydrolactoside pentaacetate, 2,3-desoxylactoside, glucouronate, N-acetylglucosamine. In one embodiment, the present invention contemplates the use of carbohydrate unit or units having five-membered rings, known as furanoses. In one embodiment, the present invention contemplates the use of carbohydrate unit or units having six-membered rings, known as pyranoses. Combinations of furanoses and pyranoses are also contemplated.

In one embodiment, an analog of the present invention is a glycosylated analog of the fusidic acid molecule of FIG. 1 that has different solubility properties than fusidic acid itself.

In one embodiment, an analog of the present invention is a glycosylated analog wherein fusidic acid is glycosylated at the C-3 position. An example of an analog of the present invention is fusidic acid 3-(4,6-di-O-acetyl-2,3-dideoxy-α-D-erythro-hex-2-enopyranoside) [FSA-G-1] (See FIG. 2). Another example of an analog of the present invention is fusidic acid 3-(2,3-dideoxy-α-D-erythro-hex-2-enopyranoside) [FSA-G-2] (See FIG. 3). Another example of an analog of the present invention is fusidic acid 3-[4-O-(2,3,4,6-tetra-O-acetyl-α-D-glucopyranosyl)-6-O-acetyl-2,3-dideoxy-α-D-erythro-hex-2-enopyranoside] [FSA-M-1] (See FIG. 10). Another example of an analog of the present invention is fusidic acid 3-[4-O-(2,3,4,6-tetra-O-acetyl-β-D-galactopyranosyl)-6-O-acetyl-2,3-dideoxy-α-D-erythro-hex-2-enopyranoside] [FSA-L-1] (See FIG. 11). Another example of an analog of the present invention is fusidic acid 3-(4,6-bis-O-(chloroacetyl)-2,3-dideoxy-α-D-erythro-hex-2-enopyranoside) [FSA-ClAc-G-1] (See FIG. 12). Another example of an analog of the present invention is fusidic acid 3-[4-O-(2,3,4,6-tetra-O-(chloroacetyl)-α-D- glucopyranosyl)-6-O-(chloroacetyl)-2,3-dideoxy-α-D-erythro-hex-2-enopyranoside] [FSA-ClAc-M-1] (See FIG. 13). Another example of an analog of the present invention is fusidic acid 3-[4-O-(2,3,4,6-tetra-O-(chloroacetyl)-β-D-galactopyranosyl)-6-O-(chloroacetyl)-2,3-dideoxy-α-D-erythro-hex-2-enopyranoside] [FSA-ClAc-L-1] (See FIG. 14). Another example of an analog of the present invention is fusidic acid 3-[4-O-(α-D-glucopyranosyl)-2,3-dideoxy-α-D-erythro-hex-2-enopyranoside] [FSA-M-2] (See FIG. 15). Another example of an analog of the present invention is fusidic acid 3-[4-O-(β-D-galactopyranosyl)-2,3-dideoxy-α-D-erythro-hex-2-enopyranoside] [FSA-L-2] (See FIG. 16).

In one embodiment, an analog of the present invention is a glycosylated analog wherein the secondary hydroxyl group at position C-11 is oxidized to a carbonyl group. An example of an analog of the present invention is 11-dehydrofusidic acid 3-(4,6-di-O-acetyl-2,3-dideoxy-α-D-erythro-hex-2-enopyranoside) [FSA-G-3] (See FIG. 4). Another example of an analog of the present invention is 11-dehydrofusidic acid 3-(2,3-dideoxy-α-D-erythro-hex-2-enopyranoside) [FSA-G-4] (See FIG. 5).

In one embodiment, an analog of the present invention is a glycosylated analog wherein fusidic acid is fully reduced at the C-24 and C-25 double bond positions and the C-2 and C-3 positions of the saccharide unit directly bound to the aglycon. An example of an analog of the present invention is 24,25-dihydrofusidic acid 3-(4,6-di-O-acetyl-2,3-dideoxy-α-D-erythro-hexanopyranoside) [FSA-G-5] (See FIG. 6). Another example of an analog of the present invention is 24,25-dihydrofusidic acid 3-(2,3-dideoxy-α-D-erythro-hexanopyranoside) [FSA-G-6] (See FIG. 7). Another example of an analog of the present invention is 11-dehydro-24,25-dihydrofusidic acid 3-(4,6-di-O-acetyl-2,3-dideoxy-α-D-erythro-hexanopyranoside) [FSA-G-7] (See FIG. 8). Another example of an analog of the present invention is 11-dehydro-24,25-dihydrofusidic acid 3-(2,3-dideoxy-α-D-erythro-hexanopyranoside) [FSA-G-8] (See FIG. 9).

In one embodiment, an analog of the present invention is a fusidic acid analog that has protecting groups at positions C-3, C-11, and C-21. (See FIG. 17). In one embodiment, an analog of the present invention is a fusidic acid analog that has C-24. (See FIG. 18). In one embodiment, an analog of the present invention is a fusidic acid analog that has a protecting group at position C-21 and an hydroxyl group at position C-24. (See FIG. 19). In one embodiment, an analog of the present invention is a fusidic acid analog that has protecting groups at positions C-3, C-11, and C-21 and at position C-24 a carbohydrate unit having protecting groups. (See FIG. 20). In one embodiment, an analog of the present invention is a fusidic acid analog that has a carbohydrate unit at position C-24. (See FIG. 21). In one embodiment, an analog of the present invention is a fusidic acid analog that has a protecting group at position C-21 and at each of positions C-3 and C-24 a carbohydrate unit having protecting groups. (See FIG. 22). In one embodiment, an analog of the present invention is a fusidic acid analog that has a carbohydrate unit at each of positions C-3 and C-24. (See FIG. 23). In one embodiment, an analog of the present invention is a fusidic acid analog that has protecting groups at positions C-3, C-11, and C-21 and an hydroxyl group at position C-25. (See FIG. 24). In one embodiment, an analog of the present invention is a fusidic acid analog that has a protecting group at position C-21 and an hydroxyl group at position C-25. (See FIG. 25). In one embodiment, an analog of the present invention is a fusidic acid analog that has protecting groups at positions C-3, C-11, and C-21 and at position C-25 a carbohydrate unit having protecting groups. (See FIG. 26). In one embodiment, an analog of the present invention is a fusidic acid analog that has a carbohydrate unit at position C-25. (See FIG. 27). In one embodiment, an analog of the present invention is a fusidic acid analog that has a protecting group at position C-21 and at each of positions C-3 and C-25 a carbohydrate unit having protecting groups. (See FIG. 28). In one embodiment, an analog of the present invention is a fusidic acid analog that has a carbohydrate unit at each of positions C-3 and C-25. (See FIG. 29).

In one embodiment, an analog of the present invention is synthesized by a) providing in any order: i) unmodified fusidic acid, ii) a derivatizing reagent, and iii) a catalyst; b) reacting in any order: i) said unmodified fusidic acid, ii) said derivatizing reagent, and iii) said catalyst, under conditions such that a glycosylated analog of the fusidic acid molecule of FIG. 1 is formed having different solubility properties than unmodified fusidic acid itself.

In another embodiment, the derivatizing agents are those reagents which provide the substituents added to fusidic acid or a modified form of fusidic acid. In one embodiment, the derivatizing agent is a carbohydrate glycal. In one embodiment, the carbohydrate glycal is either glucose-derived glycal (glucal), lactose-derived glycal (lactal), or maltose-derived glycal (maltal). A catalyst, in general, is a substance which increases the rate of a chemical reaction. In one embodiment, the catalyst is $BF_3$.etherate. In one embodiment, the catalyst is a molecular diatomic halogen. In one embodiment, the molecular diatomic halogen is molecular diatomic iodine.

In one embodiment, the carbohydrate glycal is a disaccharide glycal, for example maltose glycal (maltal), and is synthesized by a) providing in any order: i) unmodified disaccharide, ii) a protecting reagent, iii) a derivatizing reagent, and iv) a reducing agent; b) reacting in any order: i) unmodified disaccharide and ii) a protecting reagent to form a protected disaccharide; c) reacting in any order: i) the protected disaccharide of step (b) and ii) a derivatizing reagent to form a derivatized protected disaccharide; d) reacting in any order: i) the derivatized protected disaccharide of step (c) and ii) an reducing agent to form a disaccharide glycal. In one embodiment, the unmodified disaccharide is maltose. In one embodiment, the unmodified disaccharide is lactose. In one embodiment, the protecting reagent is an esterifying reagent, for example acetic anhydride. In one embodiment, the derivatizing reagent is a halogenating reagent that introduces a halogen atom at the anomeric carbon atom of the carbohydrate, for example hydrobromic acid. In one embodiment, the reducing agent is $Zn/CuSO_4$.

In one embodiment, the carbohydrate glycal is an activated carbohydrate glycal. Activated glycals are those glycals which have a sufficient reactivity to readily react with fusidic acid or a modified fusidic acid to form glycosylated analogs of fusidic acid or of modified fusidic acid. Activated glycals, by definition, are not the parent glycal themselves. Activated glycals are synthesized by a) providing in any order: i) the glycal, ii) an activating reagent, and iii) a catalyst; b) reacting in any order: i) the glycal, ii) a protecting reagent, and iii) a catalyst, under conditions such that an activated carbohydrate glycal is formed. In one embodiment, the carbohydrate glycal is maltal. Activating reagents are those reagents that convert glycals into activated glyeals. In one embodiment, the activating reagent is a carboxylic acid, for example, o-anisic acid. In one embodiment, the catalyst is a molecular diatomic halogen. In one embodiment, the molecular diatomic halogen is molecular diatomic iodine.

In one embodiment, an analog of the present invention is synthesized by a) providing in any order: i) a modified fusidic acid, ii) a derivatizing reagent, and iii) a catalyst; b) reacting in any order: i) said modified fusidic acid, ii) said derivatizing reagent, and iii) said catalyst, under conditions such that a glycosylated analog of a modified form of the fusidic acid molecule of FIG. 1 is formed having different solubility properties than unmodified fusidic acid.

A modified form of fusidic acid is fusidic acid that has been modified by chemical, enzymatic, or biological means so that the modified fusidic acid may still form a glycosylated analog in the aforementioned reaction. In one embodiment, a modified form of fusidic acid is fusidic acid wherein the C-24 and C-25 positions having double bonds have been reduced to single bonds. In another embodiment, the modified form of fusidic acid is fusidic acid wherein the hydroxyl group at C-11 has been oxidized to a carbonyl group. In another embodiment, the modified form of fusidic acid is fusidic acid wherein a hydroxyl group has been introduced at the C-24 position. For this modified form of fusidic acid, the carbon at C-24 may be either one of the two epimers, R or S. This modified form of fusidic acid may consist either of an approximately equal mixture of the two optical isomers at the C-24 position or an excess of one optical isomer over the other. In another embodiment, the modified form of fusidic acid is fusidic acid wherein a hydroxyl group has been introduced at the C-25 position.

For each of these modified forms of fusidic acid, the molecule may have other modifications termed "protecting groups" which prevent any functional groups of the modified form of fusidic acid from interfering with the glycosylation reaction. It may be the case that depending on whether the modified form of fusidic acid has certain protecting groups, the modified form of fusidic acid may react with the derivatizing reagent to give a glycosylated analog of a modified form of the fusidic acid molecule having more than one carbohydrate unit bound directly through a hydroxyl group to the aglycon. In one embodiment, the protecting group is an acyl. In one embodiment the acyl is monochloroacetyl. In another embodiment, the protecting group is a methyl group.

In one embodiment, an analog of the present invention is synthesized by a) providing in any order: i) a glycosylated analog of fusidic acid having one or more protecting groups and ii) a deprotection agent; b) reacting in any order: i) said glycosylated analog of fusidic acid having one or more protecting groups and ii) the deprotecting reagent to form a glycosylated analog of fusidic acid having fewer protecting groups.

Protecting groups are those groups which prevent undesirable reactions involving unprotected functional groups. In one embodiment, protecting groups protect the terminal hydroxyl groups of a carbohydrate unit. In one embodiment, the protecting group is an acyl. In one embodiment, the acyl is acetate. In one embodiment, the acyl is monochloroacetyl. In one embodiment, the acyl is methoxyacetyl. The prefix "per" indicates that all hydroxyl groups in a particular carbohydrate unit are protected by the designated functionality. For example, a "per-(ClOAc)-glycal" will have monochloroacetyl groups bound to each hydroxyl group of the carbohydrate unit. Deprotection reagents remove protecting groups. For example, in one embodiment, reaction of a glycosylated analog of fusidic acid with carbohydrate unit or units having protecting acyl groups with a deprotection reagent gives a glycosylated analog of fusidic acid having no protecting groups, i.e., the carbohydrate unit or units have deprotected, free hydroxyl groups. This reaction is commonly known as a hydrolysis reaction. In one embodiment, the deprotecting reagent is a chemical reagent which has properties of a nucleophile. In one embodiment, the deprotecting reagent is $Ba(OH)_2$. In one embodiment, the deprotecting reagent is $NaHCO_3$. In one embodiment, the deprotecting reagent is $KHCO_3$.

In one embodiment, an analog of the present invention is synthesized by a) providing in any order: i) a glycosylated analog of a modified form of fusidic acid having one or more protecting groups and ii) a deprotection agent; b) reacting in any order: i) a glycosylated analog of a modified form of fusidic acid having one or more protecting groups and ii) the deprotecting reagent to form a glycosylated analog of a modified form of fusidic acid having fewer protecting groups.

As for the unmodified fusidic acid, protecting groups can protect the terminal hydroxyl groups of the carbohydrate unit or units. In one embodiment, protecting groups protect functional groups of the aglycon. In one embodiment, the protecting group is an acyl. In one embodiment, the acyl is monochloroacetyl. In one embodiment, the protecting group is methyl. In one embodiment, the deprotecting reagent is $Ba(OH)_2$. In one embodiment, the deprotecting reagent is $NaHCO_3$. In one embodiment, the deprotecting reagent is $KHCO_3$.

DESCRIPTION OF THE INVENTION

Figure 1:
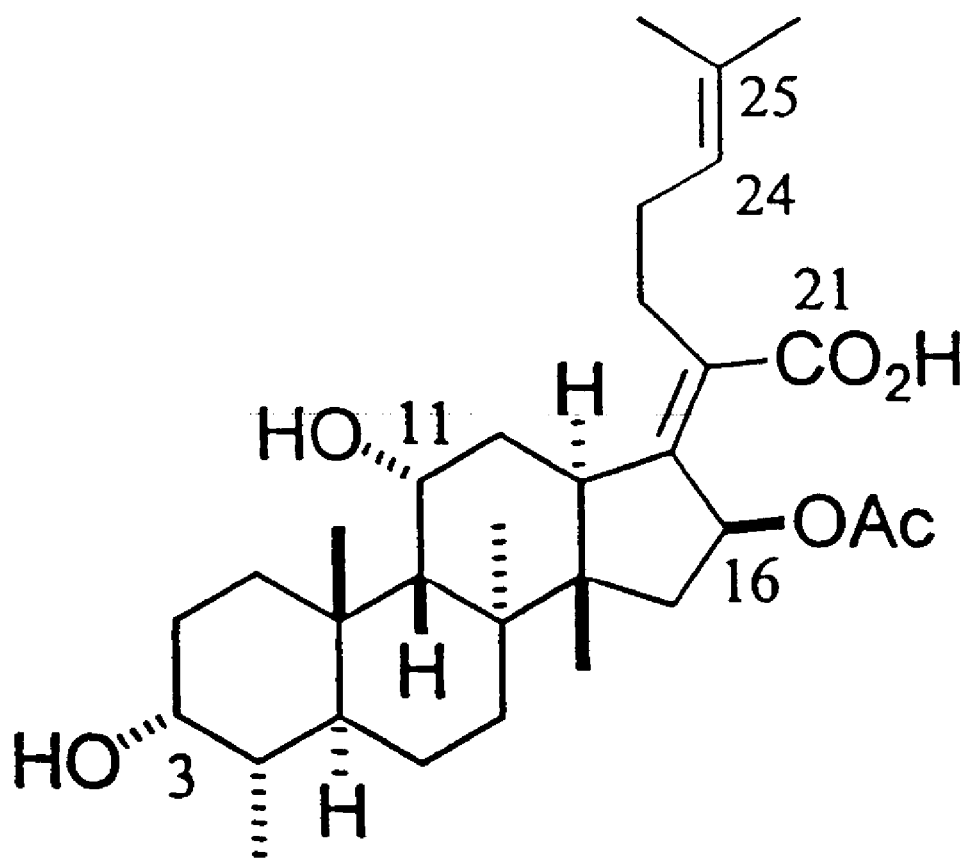
FIG. 1 shows the structure of unmodified fusidic acid.
Figure 2:
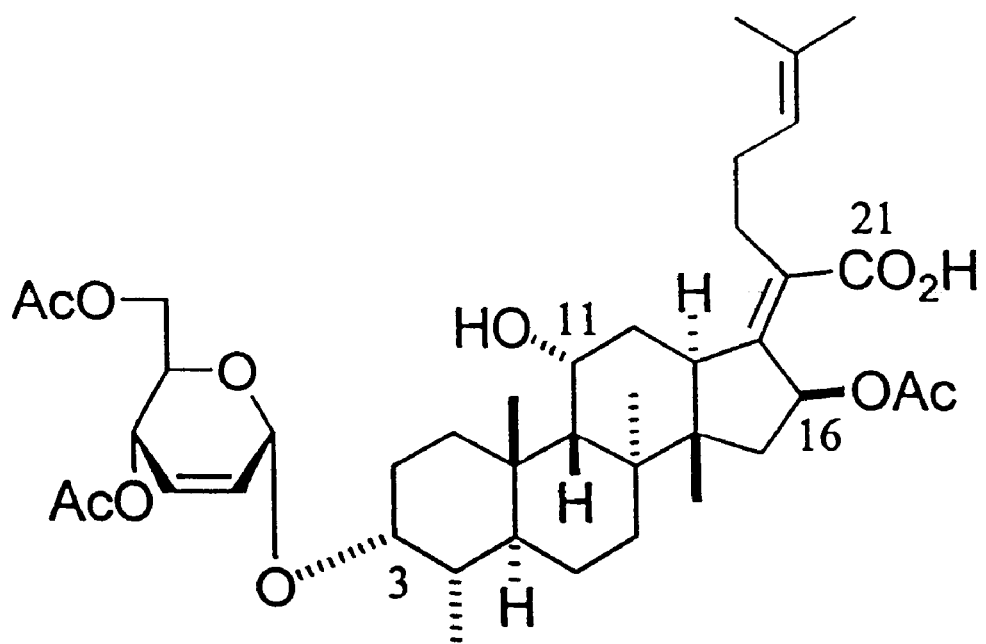
FIG. 2 shows the structure of a fusidic acid analog of the present invention: fusidic acid 3-(4,6-di-O-acetyl-2,3-dideoxy-α-D-erythro-hex-2-enopyranoside) [FSA-G-1].
Figure 3:
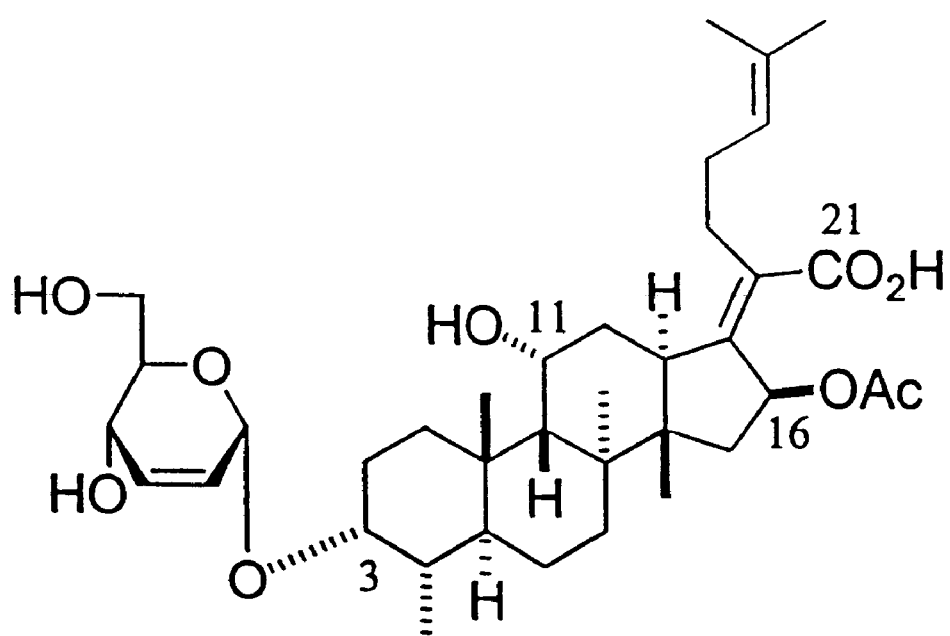
FIG. 3 shows the structure of a fusidic acid analog of the present invention: fusidic acid 3-(2,3-dideoxy-α-D-erythro-hex-2-enopyranoside) [FSA-G-2].
Figure 4:
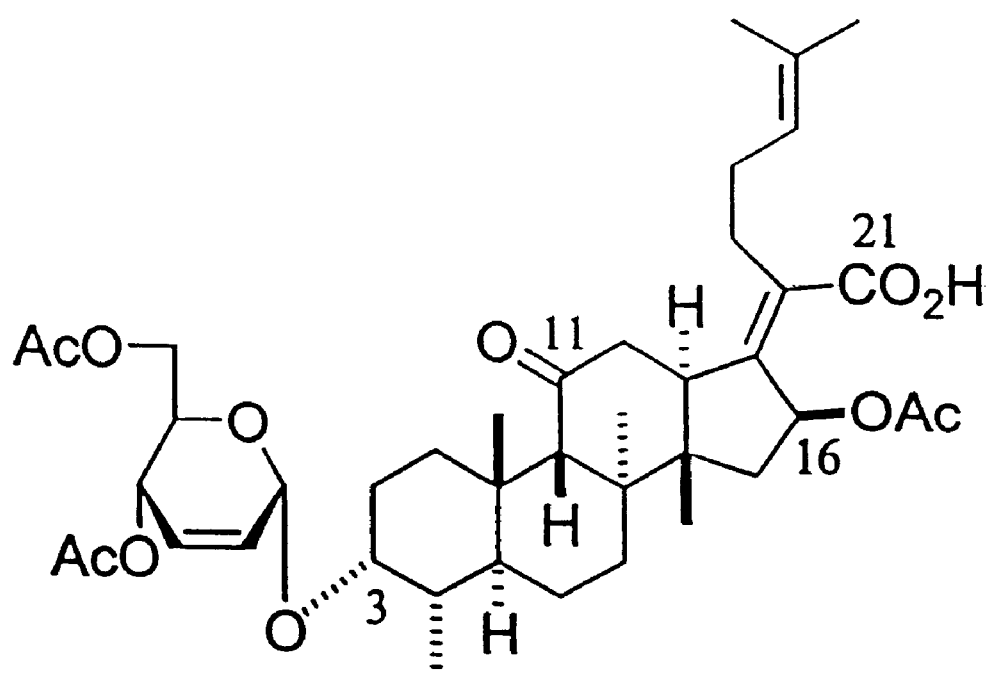
FIG. 4 shows the structure of a fusidic acid analog of the present invention: 11-dehydrofusidic acid 3-(4,6-di-O-acetyl-2,3-dideoxy-α-D-erythro-hex-2-enopyranoside) [FSA-G-3].
Figure 5:
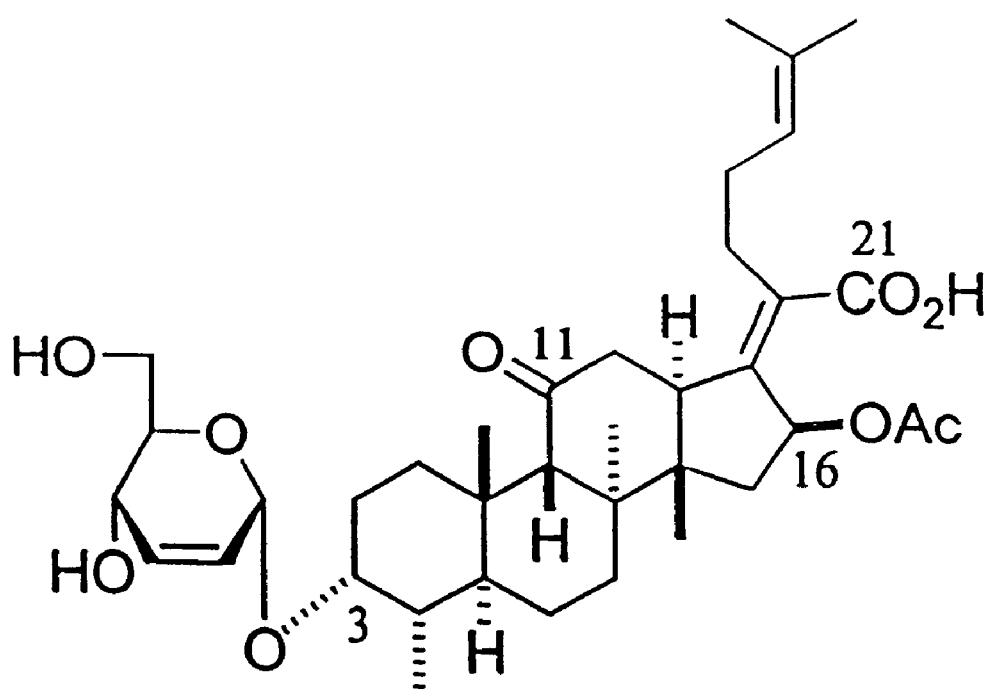
FIG. 5 shows the structure of a fusidic acid analog of the present invention: 11-dehydrofusidic acid 3-(2,3-dideoxy-α-D-erythro-hex-2-enopyranoside) [FSA-G-4].
Figure 6:
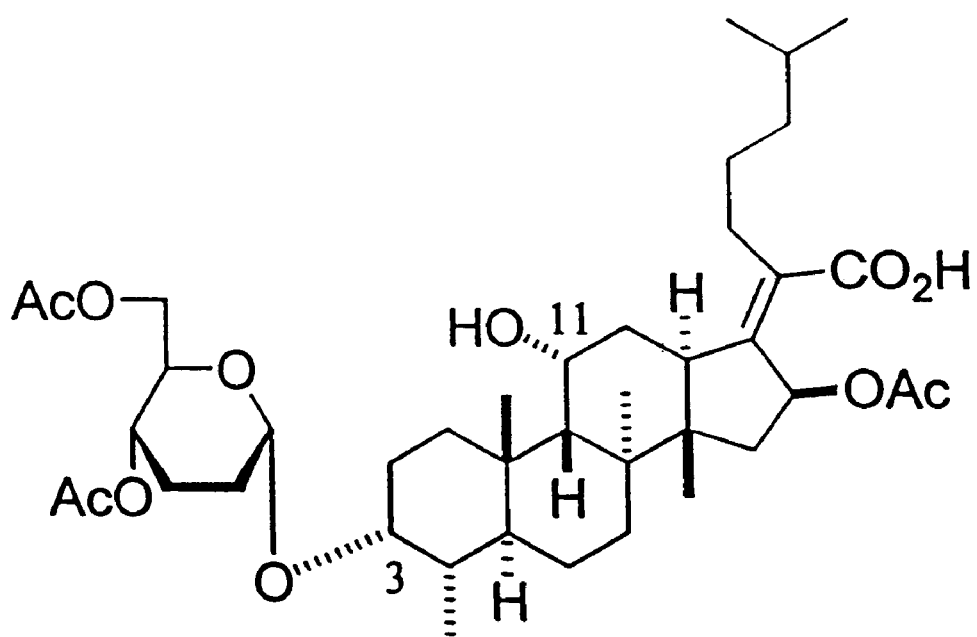
FIG. 6 shows the structure of a fusidic acid analog of the present invention: 24,25-dihydrofusidic acid 3-(4,6-di-O-acetyl-2,3-dideoxy-α-D-erythro-hexanopyranoside) [FSA-G-5].
Figure 7:
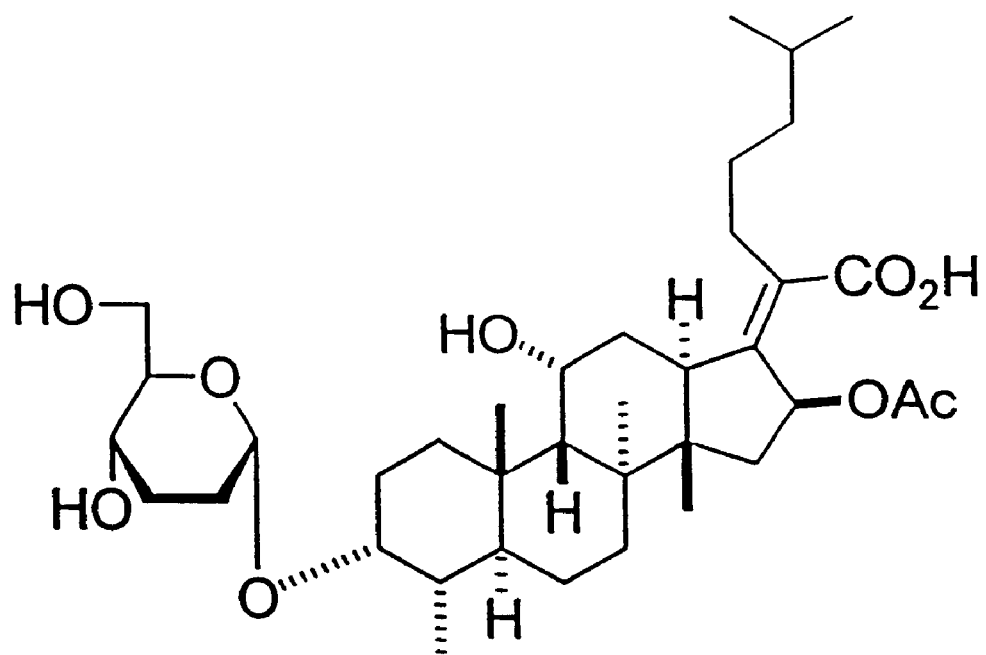
FIG. 7 shows the structure of a fusidic acid analog of the present invention: 24,25-dihydrofusidic acid 3-(2,3-dideoxy-α-D-erythro-hexanopyranoside) [FSA-G-6].
Figure 8:
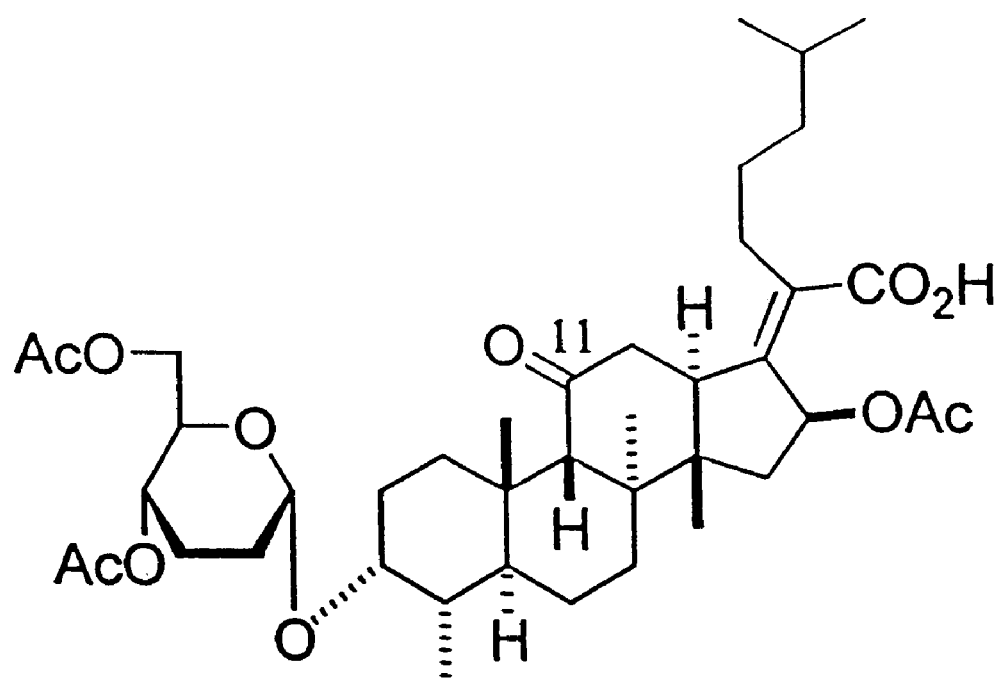
FIG. 8 shows the structure of a fusidic acid analog of the present invention: 11-dehydro-24,25-dihydrofusidic acid 3-(4,6-di-O-acetyl-2,3-dideoxy-α-D-erythro-hexanopyranoside) [FSA-G-7].
Figure 9:
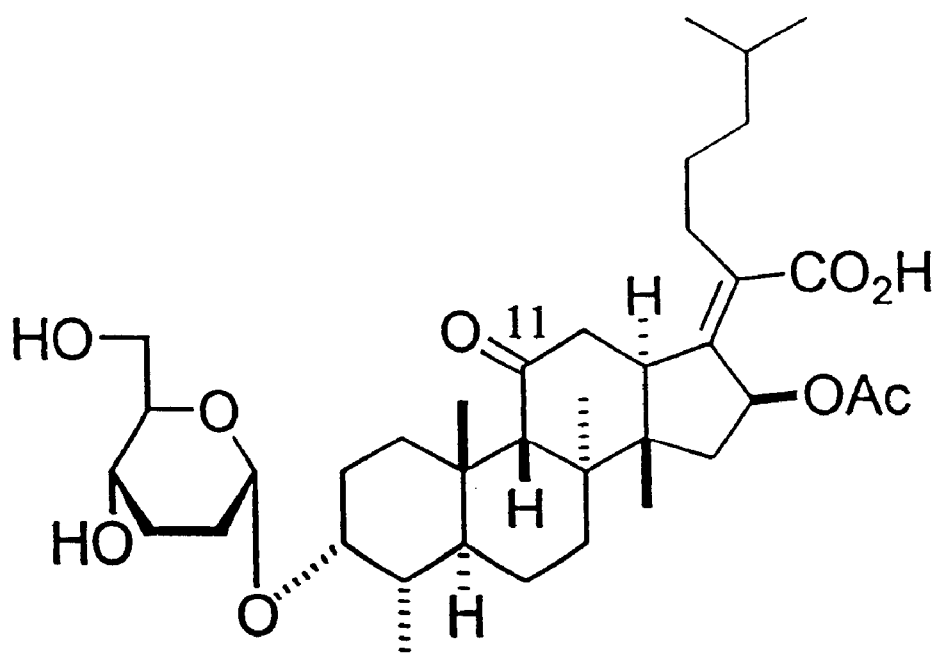
FIG. 9 shows the structure of a fusidic acid analog of the present invention: 11-dehydro-24,25-dihydrofusidic acid 3-(2,3-dideoxy-α-D-erythro-hexanopyranoside) [FSA-G-8].
Figure 10:
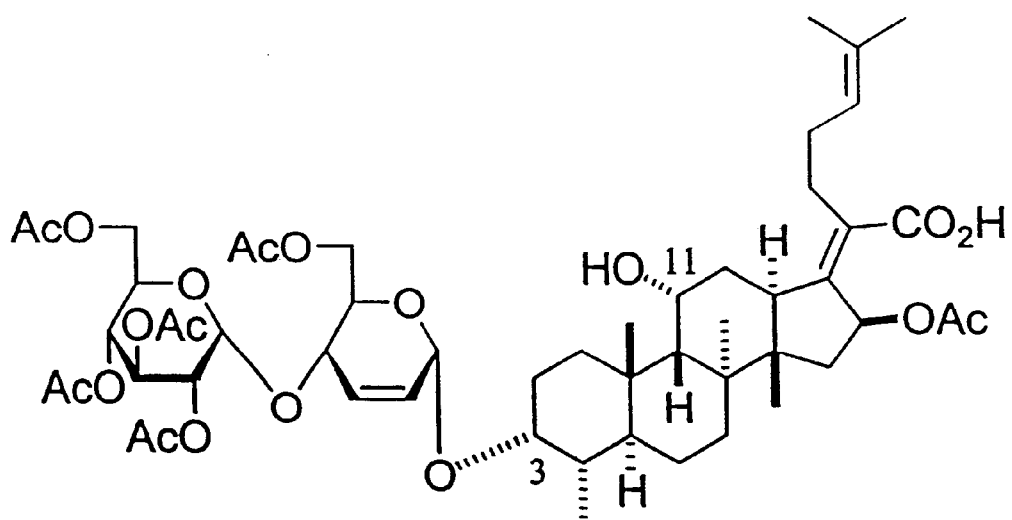
FIG. 10 shows the structure of a fusidic acid analog of the present invention: fusidic acid 3-[4-O-(2,3,4,6-tetra-O-acetyl-α-D-glucopyranosyl)-6-O-acetyl-2,3-dideoxy-α-D-erythro-hex-2-enopyranoside] [FSA-M-1].
Figure 11:
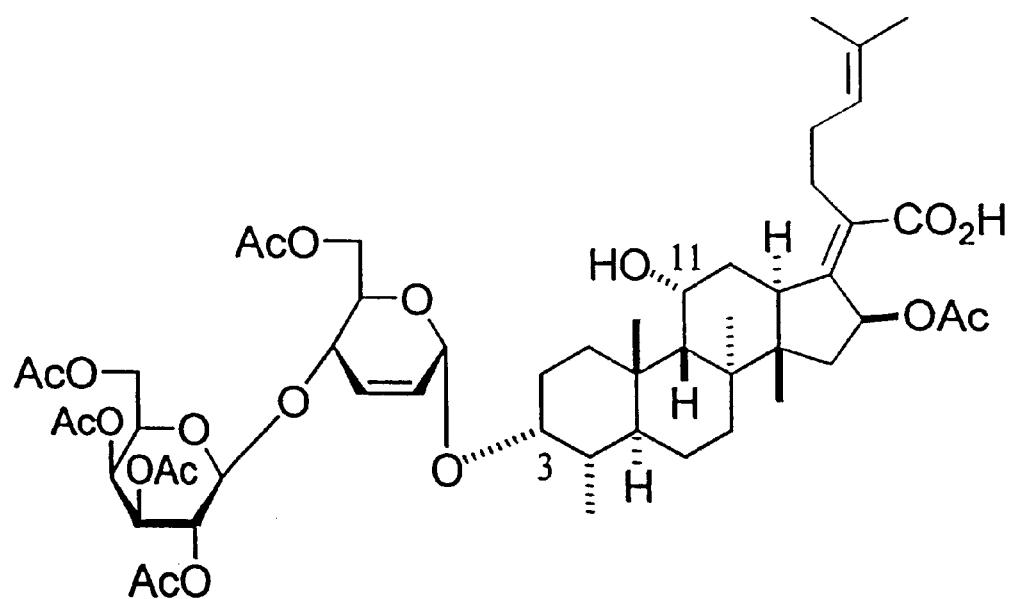
FIG. 11 shows the structure of a fusidic acid analog of the present invention: fusidic acid 3-[4-O-(2,3,4,6-tetra-O-acetyl-β-D-galactopyranosyl)-6-O-acetyl-2,3-dideoxy-α-D-erythro-hex-2-enopyranoside] [FSA-L-1].
Figure 12:
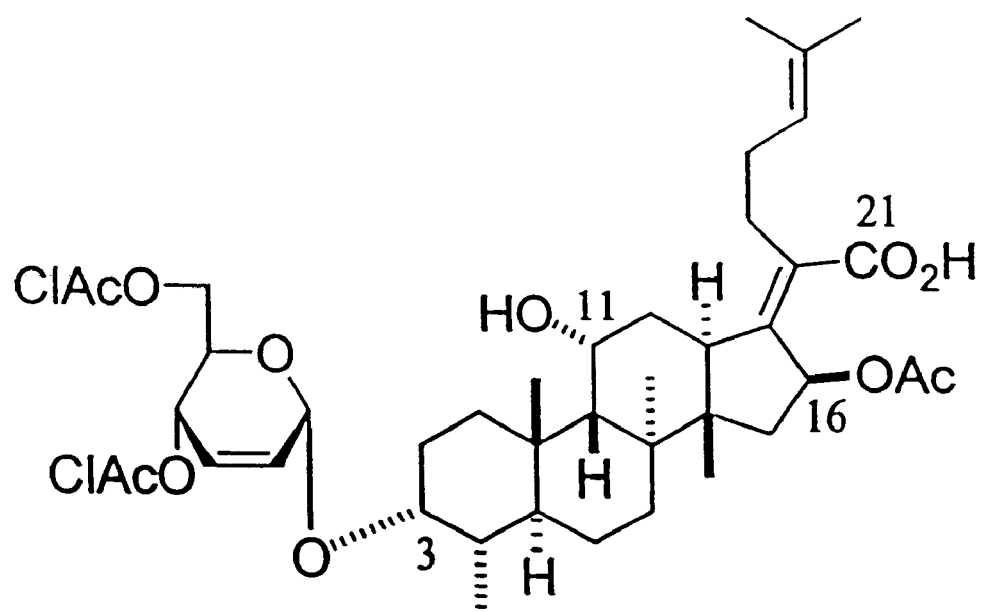
FIG. 12 shows the structure of a fusidic acid analog of the present invention: fusidic acid 3-(4,6-bis-O-(chloroacetyl)-2,3-dideoxy-α-D-erythro-hex-2-enopyranoside) [FSA-ClAc-G-1].
Figure 13:
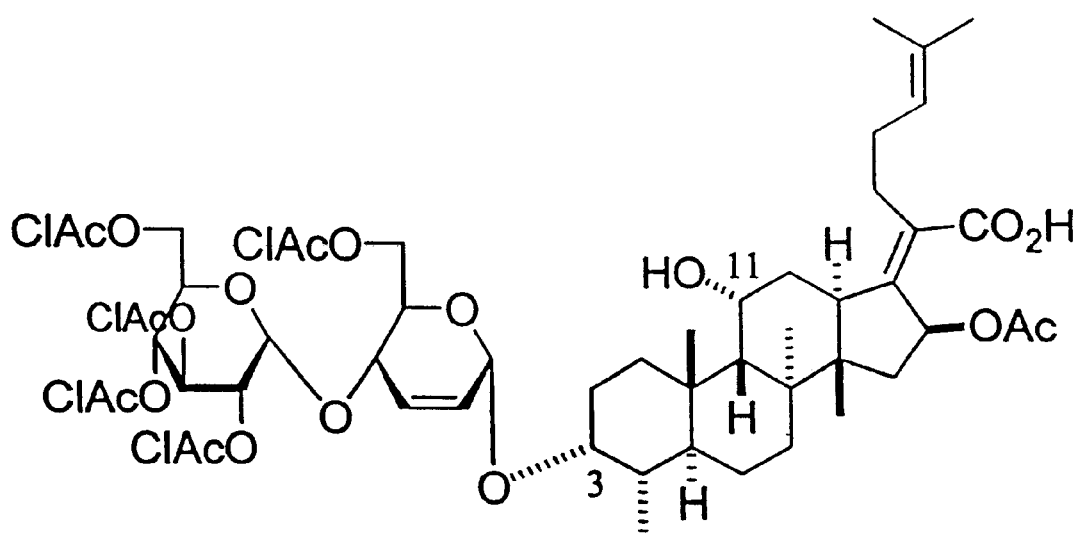
FIG. 13 shows the structure of a fusidic acid analog of the present invention: fusidic acid 3-[4-O-(2,3,4,6-tetra-O-(chloroacetyl)-α-D-glucopyranosyl)-6-O-(chloroacetyl)-2,3-dideoxy-α-D-erythro-hex-2-enopyranoside] [FSA-ClAc-M-1].
Figure 14:
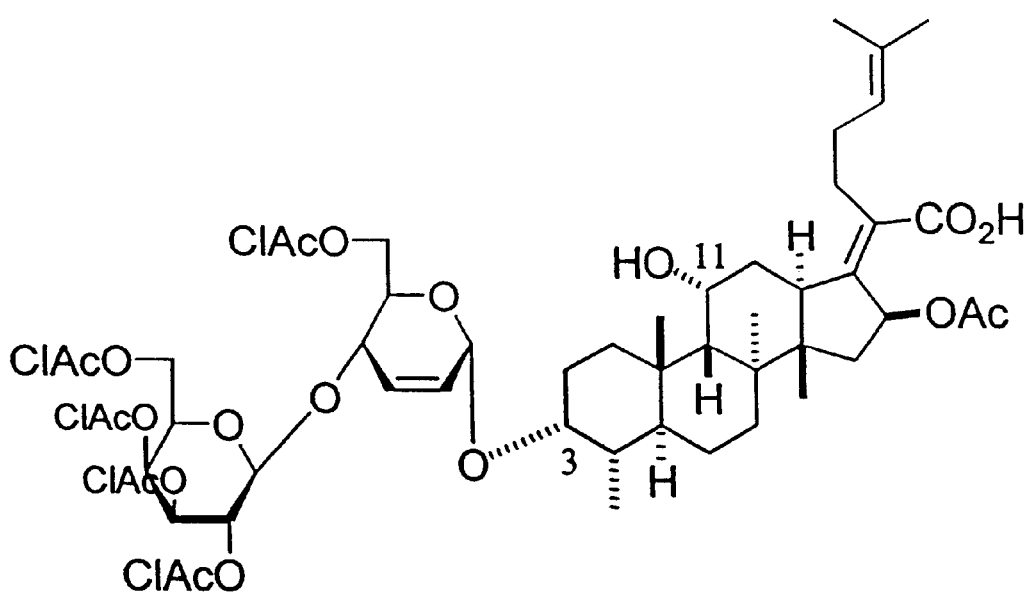
FIG. 14 shows the structure of a fusidic acid analog of the present invention: fusidic acid 3-[4-O-(2,3,4,6-tetra-O-(chloroacetyl)-β-D-galactopyranosyl)-6-O-(chloroacetyl)-2,3-dideoxy-α-D-erythro-hex-2-enopyranoside] [FSA-ClAc-L-1].
Figure 15:
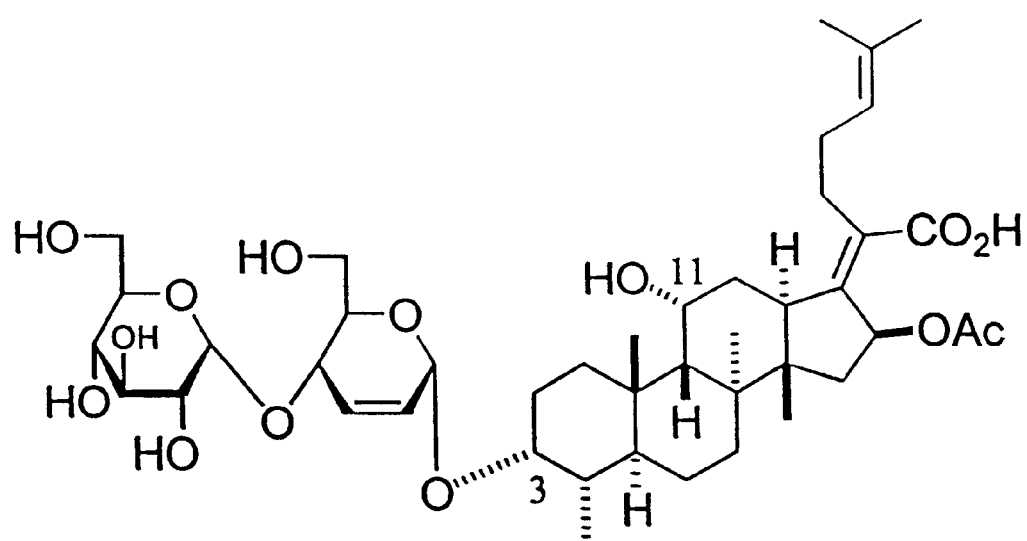
FIG. 15 shows the structure of a fusidic acid analog of the present invention: fusidic acid 3-[4-O-(α-D-glucopyranosyl)-2,3-dideoxy-α-D-erythro-hex-2-enopyranoside] [FSA-M-2].
Figure 16:
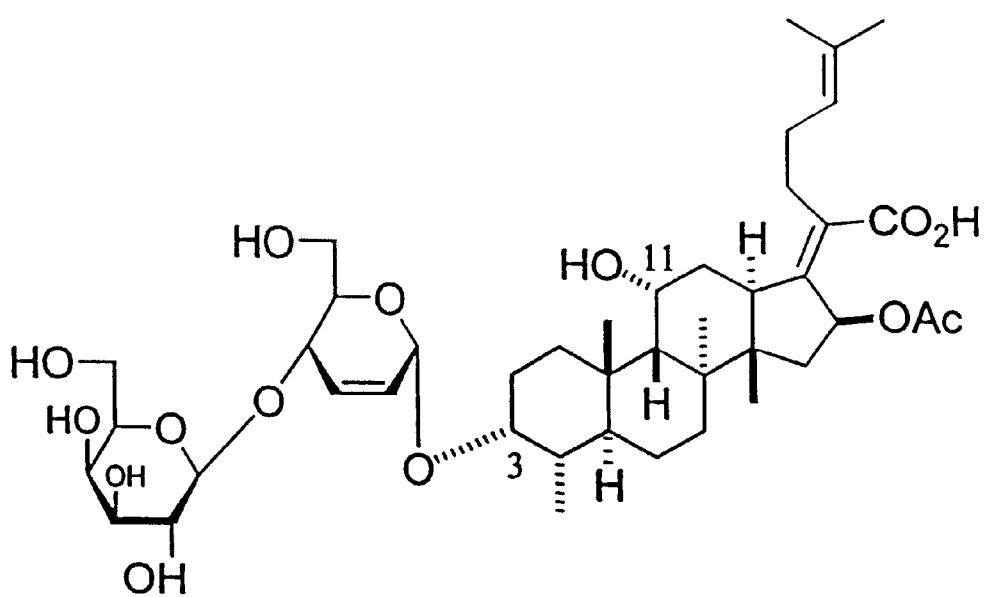
FIG. 16 shows the structure of a fusidic acid analog of the present invention: fusidic acid 3-[4-O-(β-D-galactopyranosyl)-2,3-dideoxy-α-D-erythro-hex-2-enopyranoside] [FSA-L-2].

The present invention relates to novel analogs of fusidic acid. In particular, the present invention relates to novel glycosylated analogs of fusidic acid that have different solubility properties than unmodified fusidic acid itself. The present invention also relates to glycosylated analogs of fusidic acid that act as chemotherapeutic agents. The description of the present invention involves: (I) Properties of Unmodified Fusidic Acid and Properties of Previously Modified Fusidic Acid Derivatives (Prior Art); (II) Physical Properties of Fusidic Acid Analogs of the Present Invention; (III) Synthesis of Novel Glycosylated Fusidic Acid Analogs; (IV) In Vivo Uses; (V) Methodology for Screening Glycosylated Analogs of Fusidic Acid Analogs Based on Solubility Properties.

I. Fusidic Acid and Previously Described Derivatives

The present inventors are unaware of previous efforts directed at improving the water solubility of fusidic acid by chemical derivatization of the hydroxyl groups with hydrophilic groups. Chemical modifications of fusidic acid have been, as a rule, unsuccessful at generating fusidic analogs which have improved antibacterial or antiviral activity. One of the first and most comprehensive studies of the biological effects of chemical modification of the fusidic acid molecule was undertaken by Godtfresden [See Godtfresden et al., J. Med. Chem. 9:15 (1966)]. Godtfresden and coworkers synthesized 51 derivatives of fusidic acid; none of these derivatives possessed improved antibacterial activity.

II. Physical Properties of Fusidic Acid Analogs of the Present Invention

The fusidic acid analogs of the present invention will have different solubility properties in propylene glycol as compared to unmodified fusidic acid. The different solubility properties will most likely be due to the novel carbohydrate groups attached to the relatively hydrophobic fusidic acid ring system. The present invention contemplates that those glycosylated analogs of fusidic acid prepared with derivatizing agents that are monosaccharides, i.e., the glucose-derived glycal (glucal), will have a greater solubility in solvents such as propylene glycol as compared to unmodified, fusidic acid. The present invention contemplates that those glycosylated analogs of fusidic acid prepared with derivatizing agents that have multiple saccharide units such as disaccharides, i.e., the lactose-derived glycal (lactal) or maltose-derived glycal (maltal), will have a diminished solubility in solvents such as propylene glycol as compared to unmodified fusidic acid.

In contrast, the present invention contemplates that those glycosylated analogs of fusidic acid prepared with derivatizing agents that have multiple saccharide units such as disaccharides, i.e., the lactose-derived glycal (lactal) or maltose-derived glycal (maltal), will have an increased solubility in solvents such as aqueous solutions of dextrose as compared to unmodified fusidic acid.

III. Synthesis of Novel Glycosylated Fusidic Acid Analogs

Recent developments in the area of pharmaceutical science have centered around efforts to increase the bioavailability of known drugs by chemical derivatization [See Brown and Thomas, Aust. J. Pharm. Sci. 8:1 (1979); Ji et al., J. Med. Chem. 33:2264 (1990); Stella et al., J. Med. Chem. 35:145 (1992); and, Kleeman et al., J. Med. Chem. 35:559 (1992)]. One approach is to develop methods of glycosylating a variety of medicinally-important compounds with the objective of increasing aqueous solubility while hopefully enhancing the pharmacological profile of these agents. Such a process could unlock the benefits of a broad array of biologically-active compounds with intrinsically modest hydrophilicity.

The chemistry of glycals is perfectly suited for addressing the above issues. Glycals, cyclic sugar derivatives containing a 1,2-double bond, are indispensable synthetic precursors in the field of carbohydrate chemistry. Though this class of sugars was discovered by Fischer 80 years ago [See Fischer and Zach, Preuss. Akad. Wiss. 16:3311 (1913)], there has recently been an immense volume of research using these compounds to synthesize complex polysaccharides and glycosylated products.

One reaction in particular, discovered by Ferrier in 1969 [See Ferrier, J. Chem. Soc. C 570 (1969)] and in which glycals can be attached to various nucleophiles, allows synthetic chemists to attach carbohydrates to a variety of non-carbohydrate organic molecules. The resulting compound is an O-glycoside in which a carbohydrate unit is attached to an oxygen atom of a typically hydrophobic aglycon (aglycon referring to a non-carbohydrate portion of a molecule). Although similar glycosylation reactions had been accomplished thermally using water, alcohols and phenols [See Helferich, Adv. Carbohydrate Chem. 7:209 (1952); Ferrier, J. Chem Soc. 5443 (1964); and, Ferrier et al, J. Chem Soc. 3667 (1962)], the Ferrier reaction's use of boron trifluoride etherate greatly expanded the synthetic scope.

Despite its utility, the Ferrier reaction has been less successfully applied to the commercial glycosylation of medicinally useful compounds. Such reactions, preferably performed on a large scale, require the use of Lewis acid catalysts which are more efficient, less toxic, and less harsh toward the aglycon. For example, since most of these strong Lewis acids spontaneously react with air and moisture, the use of these Lewis acids presents serious problems when handling them, particularly in the large-scale, industrial setting. For these reasons, the use of the non-toxic, stable catalyst iodine, which is an extremely mild Lewis acid and yet according to the invention retains enough acidity to effect glycosylation, is the preferred reagent. [See U.S. Pat. No. 5,278,296, hereby incorporated by reference; pending U.S. patent application Ser. No. 08/251,869, hereby incorporated by reference; and, pending U.S. patent application Ser. No. 08/429,941, hereby incorporated by reference.]

In one preferred aspect, the invention concerns O-glycoside compounds obtained by reacting an oxygen nucleophile compound and a glycosylating agent selected from 3-acylated five- and six-membered glycals in the presence of a catalytic amount of iodine (5-50 mol % with 20 mol % being the most representative) to provide a reaction mixture containing the glycosylated product.

The present invention contemplates the preparation of the necessary glycals by the following procedure. First, the desired carbohydrate may be obtained commercially in non-acetylated form and acetylated by reaction with acetic anhydride in acetic acid with a catalytic amount of hydrobromic acid. The acetylated carbohydrate is thereafter converted to an acetylated carbohydrate halide (e.g., bromide, by reaction with hydrobromic acid in acetic acid). The acetylated carbohydrate halide is converted to the acetylated glycal by reaction with $Zn/CuSO_4$. The acetylated glycal can be converted into the more reactive o-anisoyl derivatives by reaction with o-anisic acid (2-methoxybenzoic acid).

Glycals having substituted acetyl protecting groups can be prepared by first hydrolyzing the unsubstituted acetates of the glycals. Sodium methoxide or ammonia in methanol can be used for this purpose. Subsequent reaction of the unprotected glycals with the appropriate reagents will give the desired protected glycals having substituted acetyl groups. In the case of per monochloroacetyl glycals, reaction of the unprotected glycal with monochloroacetyl chloride and pyridine gives the glycal protected by monochloroacetyl groups. In the case of permethoxyacetyl glycals, reaction of the deprotected glycal with dicyclohexylcarbodiimide, 4-(dimethylamino)pyridine, and methoxyacetic acid gives the glycal protected by methoxyacetyl groups. Other glycals having substituted acetyl protecting groups can be prepared in a similar fashion. These glycals, which are considered derivatizing agents, are then reacted with fusidic acid or a modified form of fusidic acid. Alternatively, a commercially available acetylated carbohydrate may be used and thereby obviate the need for the initial reaction step.

Figure 30:
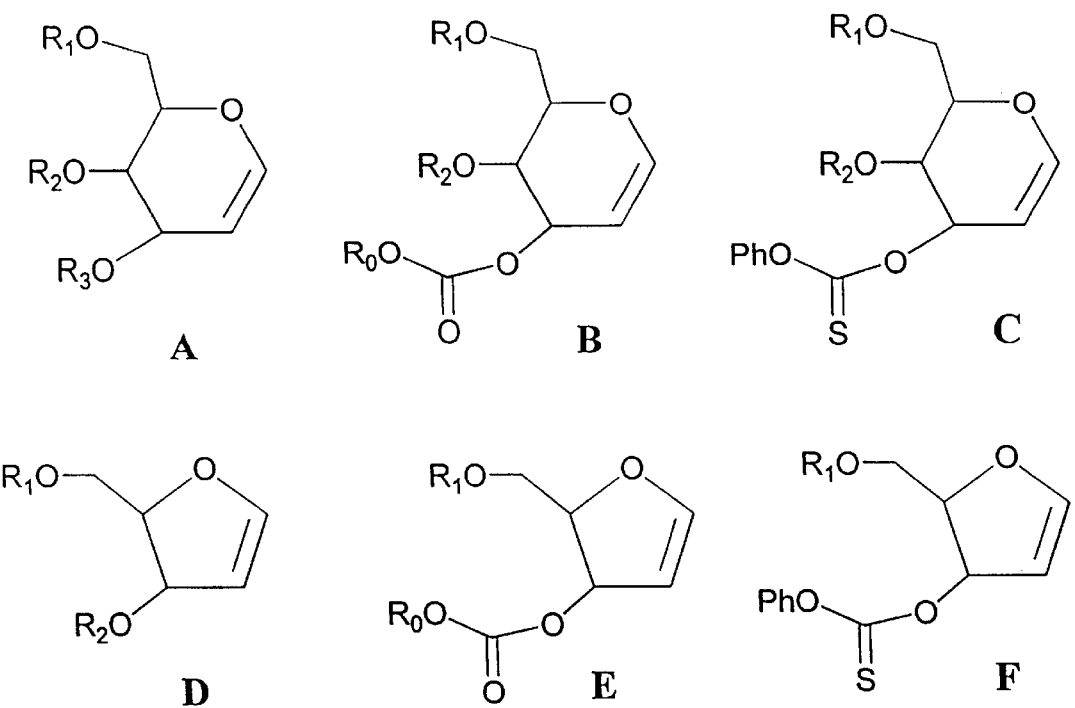
FIG. 30 shows the structure of various glycals contemplated by the present invention that can be used as derivatizing agents.

For glycosylation, preferred glycals of the formulas A-F are illustrated in FIG. 30, where $R_0$ is a lower alkyl group. $R_1$, $R_2$, and $R_3$ are the same or different and represent an aliphatic acyl group, an aromatic acyl group such as a benzoyl group, or, in the case of either $R_1$ or $R_2$, a carbohydrate unit.

Any of various suitable solvents can be used for the glycosylation reaction of which THF, acetone, diethyl ether, methylene chloride, chloroform, and benzene are preferred. The reaction temperature and time can be varied, e.g., ranging from −78° C. to room temperature for about 0.5 to 12 hours.

In another preferred aspect, the present invention contemplates partly and completely deprotected glycosylated analogs of fusidic acid and glycosylated analogs of a modified fusidic acid. These deprotected products are produced by hydrolysis of one or more acyl groups from the acylated glycosylated analogs by a deprotection agent. Deprotecting glycosylated analogs of fusidic acid or glycosylated analogs of modified fusidic acid must be done with care so as not to hydrolyze the acetate at C-16, a functionality that occurs naturally in fusidic acid and is essential for biological activity of fusidic acid. [See Godtfresden et al., J. Med. Chem. 9:15 (1966)].

In one embodiment, when the carbohydrate unit or units have unsubstituted acetyl groups, then $Ba(OH)_2$ in methanol will hydrolyze the acetyl groups of the carbohydrate unit or units to give the free alcohol and carboxylic acid. When the carbohydrate unit or units have monochloro-substituted acetyl groups, then $NaHCO_3$ or $KHCO_3$ in methanol and water will hydrolyze the acyl groups to give the unprotected, free alcohol. Under either of these conditions, the acetyl group at C-16 of the aglycon present in unmodified and underivatized fusidic acid will not be hydrolyzed.

In one embodiment, the present invention contemplates introducing a new hydroxyl functionality into unmodified fusidic acid. Before oxidizing the C-24, C-25 double bond of fusidic acid, the hydroxyl groups at C-3 and C-11 and the C-21 carboxylic acid group must be protected with appropriate protecting groups. In one embodiment, acylation of the hydroxyl groups of fusidic acid gives monochloroacetates at C-3 and C-11. In one embodiment, methylation of the C-21 carboxylic acid of fusidic acid with diazomethane gives its methyl ester derivative.

In one embodiment, the hydroxyl group can be added at C-24 through hydroboration chemistry. The resulting product will have a chiral center at C-24. If an achiral hydroboration reagent is employed, then the resulting chiral center at C-24 will consist of an epimeric mixture. Alternatively, the judicious choice of chiral hydroboration reagents followed by oxidative cleavage of the resulting carbon-boron bond can provide either the R or S epimer. In one embodiment, reaction of the hydroxyl group of the modified aglycon with a glycal will give a glycosylated analog of modified fusidic acid having a carbohydrate unit at position C-24. In one embodiment, subsequent hydrolysis of the protecting groups introduced to the aglycon and the protecting groups of the carbohydrate unit will give a glycosylated analog of modified fusidic acid having no protecting groups.

In another embodiment, the hydroxyl group can be added at C-25 through the use of oxymercuration chemistry. In one embodiment, reaction of the hydroxyl group of the modified aglycon with a glycal will give a glycosylated analog of modified fusidic acid having a carbohydrate unit at position C-25. In one embodiment, subsequent hydrolysis of the protecting groups introduced to the aglycon and the protecting groups of the carbohydrate unit will give a glycosylated analog of modified fusidic acid having no protecting groups.

In another embodiment, the protecting groups at C-3 and C-11 can be hydrolyzed after introduction of the hydroxyl functionality at either C-24 or C-25 by treatment with a base. In one embodiment, the base is $NaHCO_3$. In one embodiment, the base is $KHCO_3$. In one embodiment, reaction of the modified fusidic acid having unprotected hydroxyl groups at C-3 and C-24 with glycal will give a glycosylated analog of fusidic acid having a carbohydrate unit at each of positions C-3 and C-24. In one embodiment, subsequent hydrolysis of the protecting group at C-21 of the aglycon and the protecting groups of the carbohydrate units will give a glycosylated analog of modified fusidic acid having no protecting groups. In another embodiment, reaction of the modified fusidic acid having unprotected hydroxyl groups at C-3 and C-25 with glycal will give a glycosylated analog of fusidic acid having a carbohydrate unit at each of positions C-3 and C-25. In one embodiment, subsequent hydrolysis of the protecting group at C-21 of the aglycon and the protecting groups of the carbohydrate units will give a glycosylated analog of modified fusidic acid having no protecting groups.

IV. In Vivo Uses

The present invention contemplates using therapeutic compositions of soluble fusidic acid analogs. It is not intended that the present invention be limited by the particular nature of the therapeutic preparation. For example, such compositions can be provided together with physiologically tolerable liquid, gel or solid carriers, diluents, adjuvants and excipient. In addition, fusidic acid analogs may be used together with other chemotherapeutic agents, including unmodified fusidic acid.

With respect to the mode of administration, the fusidic acid analogs may be employed for intravenous, intramuscular, intrathecal or topical (including topical ophthalmic) administration. Formulations for such administrations may comprise an effective amount of fusidic acid analog in sterile water or physiological saline.

On the other hand, formulations may contain such normally employed additives as binders, fillers, carriers, preservatives, stabilizing agents, emulsifiers, buffers and excipient as, for example, pharmaceutical grades of mannitol, lactose, starch, magnesium stearate, sodium saccharin, cellulose, magnesium carbonate, and the like. These compositions typically contain 1%–95% of active ingredient, preferably 2%–70%.

The compositions can be prepared as injectables, either as liquid solutions or suspensions; solid forms suitable for solution in, or suspension in, liquid prior to injection may also be prepared.

The fusidic acid analogs of the present invention are often mixed with diluents or excipient which are compatible and physiologically tolerable. Suitable diluents and excipient are, for example, water, saline, ethylene glycol, dextrose, glycerol, or the like, and combinations thereof. One preferred choice is propylene glycol. A second preferred choice is aqueous solutions of dextrose. In addition, if desired the compositions may contain minor amounts of auxiliary substances such as wetting or emulsifying agents, stabilizing or pH buffering agents.

Options for optimal method of fusidic acid analog administration include, but are not limited to: a 30-minute infusion every three weeks, a 30-minute infusion daily×5 every three weeks, a 24-hour infusion every three weeks, a 120-hour infusion every three weeks, and a 72-hour infusion repeated every three weeks.

Likewise, dosage ranges for fusidic acid analog treatment include, but are not limited to: 1 to 50 $mg/m^2/day$.

V. Methodology for Screening Glycosylated Analogs of Fusidic Acid Analogs Based on Solubility Properties.

We claim glycosylated analogs of fusidic acid. These compounds may be prepared by either glycosylation of fusidic acid itself or a modified form of fusidic acid, and once glycosylated, the glycosylated analogs may undergo a number of subsequent modifications. This section outlines a procedure whereby a novel glycosylated analog of fusidic acid can be screened for desired solubility properties. These desired solubility properties consist of an increased solubility of the glycosylated analog as compared to unmodified fusidic acid in different diluents or excipient. The present invention contemplates the use of propylene glycol as a diluent or excipient. The present invention contemplates the use of aqueous solutions of dextrose as a diluent or excipient.

This screening procedure is proposed without intending to be limited to the mechanism by which enhanced solubility is achieved in different diluents or excipient. The present screening method also contemplates the use of aqueous solutions with the diluents or excipient. These aqueous solutions can be buffers, saline solution, or other aqueous solutions having auxiliary substances.

Screening Procedure:

Mode I: Determine whether the aglycon unit of the glycosylated analog of fusidic acid of interest possesses at least one hydroxyl functional group which can be glycosylated with the glycal of interest.

Mode II: Determine whether the glycosylated analog of fusidic acid has enhanced solubility properties in propylene glycol as compared to fusidic acid.

Mode III: Determine whether the glycosylated analog of fusidic acid has enhanced solubility properties in aqueous solutions of dextrose as compared to fusidic acid.

A new glycosylated analog of fusidic acid can be evaluated for the desired solubility properties in propylene glycol according to the procedure outlined in Table 1.

TABLE 1

Evaluation of Solubility Properties of Novel Glycosylated Analogs of Fusidic Acid

| Mode | Result | INTERPRETATION/NEXT STEP |
| --- | --- | --- |
| I | + react | Glycosylation of aglycon unit of proposed glycosylated analog of fusidic acid is readily carried out. Perform glycosylation reaction (and any other necessary modifications) and evaluate according to Mode II. |

TABLE 1-continued

Evaluation of Solubility Properties of Novel Glycosylated Analogs of Fusidic Acid

| Mode | Result | INTERPRETATION/NEXT STEP |
|---|---|---|
| | − react | Glycosylation of aglycon unit of proposed glycosylated analog of fusidic acid is not readily carried out and should not be further evaluated. |
| II | + sol | Glycosylated analog of fusidic acid has enhanced solubility properties in propylene glycol as compared to unmodified fusidic acid. The glycosylated analog of fusidic acid is useful. |
| | − sol | Glycosylated analog of fusidic acid has similar or diminished solubility properties in propylene glycol as compared to unmodified fusidic acid. Evaluate according to Mode III. |
| III | + sol | Glycosylated analog of fusidic acid has enhanced solubility properties in aqueous solutions of dextrose as compared to unmodified fusidic acid. The glycosylated analog of fusidic acid is useful. |
| | − sol | Glycosylated analog of fusidic acid has similar or diminished solubility properties in aqueous solutions as compared to unmodified fusidic acid. The glycosylated analog of fusidic acid is not useful. |

Key:
+ react = glycosylation reaction possible;
− react = glycosylation reaction not possible;
+ sol = enhanced solubility as compared to unmodified fusidic acid;
− sol = similar or diminished solubility as compared to unmodified fusidic acid.

Experimental

The following examples serve to illustrate certain preferred embodiments and aspects of the present invention and are not to be construed as limiting the scope thereof.

In the experimental disclosure which follows, the following abbreviations apply: equiv (equivalents); M (molar); μM (micromolar); N (normal); mol (moles); mmol (millimoles); μmol (micromoles); nmol (nanomoles); g or gm (grams); mg (milligrams); μg (micrograms); L (liters); mL (milliliters); μL (microliters); cm (centimeters); mm (millimeters); μm (micrometers); nm (nanometers); ° C. (degrees Centigrade); TLC (thin layer chromatography); DMF (N,N-dimethylformamide); THF (tetrahydrofuran); Ac (—C(═O)CH₃); ClAc (—C(═O)CH₂Cl); Ph (a phenyl group, or —C₆H₅).

Compounds may be referred to by abbreviated names. For example, 2,4,6-tri-O-acetyl-D-glucal may be identified as tri-O-acetyl-D-glucal, tri-O-acetyl-glucal, tri-acetyl-D-glucal, or tri-acetyl glucal. The glycals derived from other sugars such as maltal and lactal will have similar variations on their nomenclature.

The Experimental has been broadly divided into three sections: I. Screening Experimental on the Basis of Solubility Properties; II. Synthesis of Reactants; III. Synthesis of Novel Analogs.

I. Screening Experimental on the Basis of Solubility Properties

The solubility properties of the glycosylated analogs of fusidic acid of the present invention will be measured in the diluent or excipient of choice by a spectrophotometric assay. An appropriate amount of the glycosylated analog of fusidic acid will be suspended in 1 mL of the diluent or excipient of choice in a 1.5 mL cryovial. The suspensions will be mixed continuously on a Thermolyne vari-mix at room temperature for 24 hr. The suspensions then will be centrifuged at 14,000×g for 2 minutes to separate the undissolved materials. The supernatant fluids will be diluted appropriately with the diluent or excipient of choice and the ultraviolet spectrums will be recorded on a Beckman 640 DU spectrophotometer. For comparison, a standard stock solution will be prepared for each glycosylated analog of fusidic acid in a solvent in which the compound is readily soluble. The ultraviolet spectrum will be measured. The solubility of each glycosylated analog of fusidic acid in the solvent of choice will be calculated based on the following formula:

$$C_{unknown} = C_{standard} \times (A_{unknown} \times D_{dilution})/A_{standard}$$

where $C_{unknown}$ is the concentration of the unknown solution to be determined; $C_{standard}$ is the concentration of the standard working solution; $A_{standard}$ is the absorbance at the appropriate wavelength of the standard working solution; $D_{dilution}$ is the appropriate dilution factor used so that the absorbance of the unknown working solution is within the dynamic range of the UV spectrophotometer (usually less than 1.25 absorbance units). The same assay will be conducted for fusidic acid in the excipient or diluent of choice, so that a $C_{unknown}$ for unmodified fusidic acid will be determined in each diluent or excipient of choice.

The solubility properties of the glycosylated analogs of fusidic acid will be compared to the solubility property of unmodified fusidic acid in the diluent or excipient of choice by comparing the $C_{unknown}$ values that will have been determined from the assay. Those glycosylated analogs of fusidic acid that have a $C_{unknown}$ that is greater than 1.1 times the $C_{unknown}$ of unmodified fusidic acid in the diluent or excipient of choice will be deemed to have enhanced solubility properties. Those glycosylated analogs of fusidic acid that have a $C_{unknown}$ that is less than or equal to 1.1 times the $C_{unknown}$ of unmodified fusidic acid and greater than or equal to 0.9 times the $C_{unknown}$ of unmodified fusidic acid in the diluent or excipient of choice will be deemed to have similar solubility properties. And those glycosylated analogs of fusidic acid that have a $C_{unknown}$ that is less than 0.9 times the $C_{unknown}$ of unmodified fusidic acid in the diluent or excipient of choice will be deemed to have diminished solubility properties.

II. Synthesis of Reactants

EXAMPLE 1

This example describes the synthesis of tri-O-(chloroacetyl)-glucal. Bouhroum and Vottero have reported the prepation of this compound. [See Bouhroum and Vottero, Tetra. Letts. 31:7441 (1990)]. To a solution of tri-O-acetyl-glucal (18.0 g) in 150 mL of methanol was added 10 mL of 25% sodium methoxide in methanol. The reaction mixture was stirred for 6 h at room temperature, whereupon the solvent was removed and the resultant oil was dissolved by first adding 100 mL of methanol and then 400 mL of THF. The solution was dried over anhydrous sodium sulfate, filtered, and concentrated to give 8.78 g (91%) of a yellowish semi-solid. A portion of this product (3.26 g) was dissolved in 150 mL of THF and 15 g of pyridine, cooled to 0° C., and 8.32 g of chloroacetyl chloride added. The solution was then allowed to warm to room temperature and was stirred overnight. The reaction mixture was then poured into 100 mL of ether and washed with 100 mL of water, 100 mL of saturated NaHCO₃, 100 mL of saturated aqueous CuSO₄, 50 mL of brine, dried over Na₂SO₄, filtered and concentrated under reduced pressure. Silica gel chromatography (30% ethyl acetate in hexanes) of the crude oil provided 6.01 g (64%) of tri-O-(chloroacetyl)-glucal as a yellowish oil.

$[\alpha]_D^{20}$ −7.4° (c=1.00, CHCl₃); ¹H NMR (360 MHz, CDCl₃) δ 4.08 (s, 2H), 4.11 (s, 2H), 4.14 (s, 2H), 4.38 (m, 2H), 4.52 (dd, J=12.9, 6.2 Hz, 1H), 4.90 (dd, J=6.2, 3.3 Hz, 1H), 5.32 (dd, J=8.0, 6.2 Hz, 1H), 5.48 (m, 1H), 6.53 (dd, J=6.2, 1.1 Hz, 1H); $^{13}$C NMR (90 MHz, CDCl$_3$) δ 40.53 (t), 40.64 (t), 40.75 (t), 62.57 (t), 68.49 (d), 68.98 (d), 73.29 (d), 98.12 (d), 146.37 (d), 166.32 (s), 166.87 (s), 166.99 (s); IR (neat) 789 (w), 927 (w), 967 (w), 1026 (w), 1065 (w), 1104 (m), 1165 (s), 1247 (m), 1287 (m), 1315 (m), 1411 (w), 1649 (w), 1763 (s), 2962 (w) cm$^{-1}$.

EXAMPLE 2

This example describes the synthesis of tri-O-acetyl-glucal. While the compound could be commercially obtained from Pfanstiehl Laboratories Inc. (Wankeyan, Ill.), the procedure described below has the advantage of reduced cost as compared to the commercial source.

Glucose (1.00 g) was suspended in a solution of acetic acid (10 mL) and acetic anhydride (3.61 g, 7.0 equiv) and 1.00 g of 31% HBr/acetic acid was added. The reaction mixture was stirred for 1 h, after which an additional 9.00 g of a 31% solution of HBr/acetic acid was added to give a total of 7.7 equiv of HBr, and the reaction mixture was stirred overnight. Sodium acetate was then added (2.70 g) to neutralize the excess HBr, and the reaction mixture was added to a suspension containing pulverized CuSO$_4$.5H$_2$O (0.315 g), zinc (12.6 g), water (10 mL), sodium acetate (9.450 g), and acetic acid (5 mL) and the resultant mixture was stirred vigorously for 1.5 h at room temperature. The solution was then filtered and the solid residue washed with ethyl acetate (100 mL) and water (100 mL). The organic layer of the filtrate was washed with NaHCO$_3$ (100 mL) and brine (50 mL), dried over anhydrous sodium sulfate, filtered, and the solvent removed under reduced pressure to provide tri-O-acetyl-glucal (1.35 g, 98%) as a colorless oil free of impurities as judged by $^1$H NMR.

EXAMPLE 3

This example describes the synthesis of di-O-acetyl-O-((o-methoxy)benzoyl)-glucal. Tri-O-acetyl-glucal (1.00 g) was dissolved with o-anisic acid (0.671 g, 1.2 equiv) and iodine (0.186 g, 0.2 equiv) in 45 mL of THF and the solution was quickly cooled to −78° C. A 1 mm Hg vacuum line was then attached and the reaction mixture allowed to warm slowly to −5° C. This reaction mixture was stirred for 2 h under these conditions, replacing the lost THF solvent periodically. The reaction mixture was then poured onto 50 mL of ethyl acetate and washed successively with saturated aqueous Na$_2$S$_2$O$_3$, saturated aqueous NaHCO$_3$, and brine. The organic layer was then dried over anhydrous sodium sulfate, filtered, and the solvent removed under reduced pressure. The resultant crude oil was purified by silica gel chromatography (75% ethyl acetate in hexanes) to provide di-O-acetyl-O-((o-methoxy)benzoyl)-glucal (1.14 g, 85%) as a mixture of 4 isomers. A 6:1 mixture of the α and β isomers could be separated for spectral analysis from a 1.4:1 mixture of the 3R and 3S isomers by silica gel chromatography (20% ethyl acetate in hexanes). While this experimental procedure produces isomers, under the conditions in which the isomeric mixture is subsequently added to the aglycon (see Example 27), a single intermediate will be formed resulting in a single final stereochemical product.

α anomer: TLC R$_f$ 0.56 (2:1 ethyl acetate:hexanes); [α]$_D^{20}$+18.9° (c=1.02, CHCl$_3$) $^1$H NMR (360 MHz, CDCl$_3$) δ 2.07 (s, 3H), 2.12 (s, 3H), 3.91 (s, 3H), 4.26 (m, 3H), 5.43 (ddd, J=9.5, 3.2, 1.6 Hz, 1H), 6.00 (1H) and 6.06 (1H) (ABq, J$_{AB}$=10.2 Hz, the 6.00 peaks are further split into dd with J=2.8, 1.9 Hz, the 6.06 peaks are further split into dd with J=0.8, 0.8 Hz), 6.56 (ddd, J=2.8, 0.9, 0.9 Hz, 1H), 6.99 (m, 2H), 7.51 (ddd, J=8.1, 7.5, 1.8 Hz, 1H), 7.82 (dd, J=8.1, 1.8 Hz, 1H); $^{13}$C NMR (90 MHz, CDCl$_3$) δ 20.69 (q), 20.91 (q), 55.94 (q), 62.57 (t), 64.80 (d), 69.17 (d), 88.33 (d), 112.11 (d), 119.31 (s), 120.09 (d), 126.18 (d), 130.53 (d), 131.74 (d), 159.51 (s), 164.56 (s), 170.08 (s), 170.77 (s); IR (KBr) 759 (w), 926 (m), 1044 (m), 1193 (w), 1236 (s), 1294 (w), 1371 (w), 1438 (w), 1466 (w), 1492 (w), 1601 (w), 1743 (s) cm$^{-1}$.

3R and 3S isomers: TLC R$_f$ 0.62 (2:1 ethyl acetate:hexanes); [α]$_D^{20}$+30.4° (c=1.01, CHCl$_3$); $^1$H NMR (300 MHz, CDCl$_3$) δ 2.03 (s, 3H, 3S isomer), 2.09 (s, 3H, 3R isomer), 2.09 (s, 3H, 3R isomer), 2.10 (s, 3H, 3S isomer), 3.90 (s, 3H), 4.22–4.53 (m, 3H), 5.04 (m, 1H), 5.24 (dd, J=10.1, 3.7 Hz, 1H, 3R isomer), 5.39 (dd, J=6.8, 5.8 Hz, 1H, 3S isomer), 5.54 (dd, J=4.6, 3.8 Hz, 1H, 3S isomer), 5.71 (dd, J=6.8, 3.8 Hz, 1H, 3R isomer), 6.51 (d, J=6.2 Hz, 1H, 3S isomer), 6.58 (d, J=5.9 Hz, 1H, 3R isomer), 7.00 (m, 2H), 7.49 (m, 1H), 7.78 (m, 1H); $^{13}$C NMR (90 MHz, CDCl$_3$) δ 20.74 (q, 2C), 55.95 (q), 61.64 (t, 3S isomer), 62.04 (t, 3R isomer), 66.67 (d), 67.26 (d, 3R isomer), 67.34 (d, 3S isomer), 70.78 (d, 3R isomer), 74.04 (d, 3S isomer), 97.77 (d, 3R isomer), 99.16 (d, 3S isomer), 111.98 (d, 3S isomer), 112.15 (d, 3R isomer), 119.90 (s), 120.16 (d), 131.47 (d, 3R isomer), 131.99 (d, 3S isomer), 133.73 (d, 3R isomer), 134.05 (d, 3S isomer), 145.56 (d, 3S isomer), 147.92 (d, 3R isomer), 159.30 (s), 165.36 (s), 169.54 (s), 170.69 (s); IR (KBr) 758 (w), 1076 (m), 1128 (s), 1227 (w), 1295 (w), 1369 (w), 1438, 1468 (w), 1492 (w), 1601 (w), 1647 (w), 1744 (s) cm$^{-1}$.

EXAMPLE 4

This example describes the synthesis of hexa-O-acetyl-maltal, which is not commercially available. This procedure has the advantage of using the same solvent for the entire workup. Maltose monohydrate (1.00 g of a mixture of 90% maltose, 10% glucose and maltatriose) was suspended in a solution of acetic acid (10 mL) and acetic anhydride (2.83 g, 10.0 equiv) and 1.00 g of a 31% HBr/acetic acid solution was added. The reaction mixture stirred for 1 h, after which 9.00 g more of a 31% HBr/acetic acid solution was added and allowed to stir overnight. The reaction mixture was then poured into a suspension containing pulverized CuSO$_4$.5H$_2$O (0.182 g), zinc (7.290 g), water (10 mL), sodium acetate (5.470 g), and acetic acid (5 mL) and the resultant reaction mixture was stirred vigorously for 1.5 h. The solution was then filtered and the solid washed with ethyl acetate (100 mL) and water (100 mL). The organic layer of the filtrate was then washed with NaHCO$_3$ (100 mL) and brine (50 mL), dried over anhydrous sodium sulfate, filtered and the solvent removed under reduced pressure to provide a colorless oil which was purified by silica gel chromatography (50% ethyl acetate in hexanes) to give hexa-O-acetyl-maltal (1.21 g, 86%) as a colorless solid and tri-O-acetyl-glucal (0.132 g, 88%) as a colorless oil. Regarding the maltose starting material, a more pure commercial sample would be preferred, obviating the need for the aforementioned chromatographic separation.

EXAMPLE 5

This example describes the synthesis of penta-O-acetyl-O-((o-methoxy)benzoyl)-maltal. Hexa-O-acetyl maltal (1.00 g) was dissolved with o-anisic acid (0.326 g, 1.2 equiv) and iodine (0.090 g, 0.20 equiv) in 45 mL of THF and the solution was quickly cooled to −78° C. A 1 mm Hg vacuum line was then attached and the reaction mixture was allowed to warm slowly to −5C. This reaction mixture was stirred for 3 h under these conditions, replacing the lost THF solvent periodically. The reaction mixture was then poured onto 50 mL of ethyl acetate and washed successively with saturated aqueous $Na_2S_2O_3$, saturated aqueous $NaHCO_3$, and brine. The organic layer was then dried over anhydrous sodium sulfate, filtered, and the solvent removed under reduced pressure. The resultant crude oil was purified by silica gel chromatography (75% ethyl acetate in hexanes) to provide penta-O-acetyl-O-((o-methoxy)benzoyl)-maltal (1.103 g, 95%) as a mixture of 4 isomers. An 8:1 mixture of the α and β anomers could be separated for spectral analysis from a mixture of the 3R and 3S isomers along with a small amount of starting hexa-O-acetyl-maltal by silica gel chromatography (20% ethyl acetate in hexanes).

α anomer: mp 59–60° C.; TLC $R_f$ 0.48 (2:1 ethyl acetate:hexanes); $[\alpha]_D^{20}$ +118.4° (c=1.03, $CHCl_3$); $^1H$ NMR (360 MHz, $CDCl_3$) δ 2.01 (s, 3H), 2.03 (s, 3H), 2.04 (s, 3H), 2.09 (s, 3H), 2.11 (s, 3H), 3.37–4.52 (m, 7H), 3.93 (s, 3H), 4.72–5.51 (m, 4H), 5.99 (1H) and 6.01 (1H) (ABq, $J_{AB}$= 10.3), 6.53 (br s), 7.01 (m, 2H), 7.52 (dd, J=8.2, 7.5 Hz, 1H), 7.84 (d, J=7.6 Hz, 1H); $^{13}C$ NMR (90 MHz, $CDCl_3$) δ 20.54 (q, 5C), 55.98 (q), 61.73 (t), 63.05 (t), 68.35 (d, 3C), 69.78 (d, 3C), 70.74 (d), 88.21 (d), 94.44 (d), 112.19 (d), 119.53 (s), 120.10 (d), 126.24 (d), 129.84 (d), 131.65 (d), 133.83 (d), 159.39 (s), 164.46 (s), 169.19 (s), 169.71 (s), 169.82 (s), 170.16 (s, 2C).

EXAMPLE 6

This example describes the synthesis of hexa-O-acetyl-lactal. Lactose (1.00 g) was suspended in a solution of acetic acid (10 mL) and acetic anhydride (2.68 g, 9.0 equiv) and 1.00 g of a 31% HBr/acetic acid solution was added. Although the solid lactose did not dissolve after stirring for 1 h, an additional 9.00 g of a 31% HBr/acetic acid solution was added to the reaction mixture and the solution was stirred overnight at room temperature. The reaction mixture was then poured onto a suspension containing pulverized $CuSO_4 \cdot 5H_2O$ (0.182 g), zinc (7.29 g), water (10 mL), sodium acetate (5.47 g), and acetic acid (5 mL), and the resultant reaction mixture was stirred vigorously for 1.5 h. The solution was then filtered and the solid residue washed with ethyl acetate (100 mL) and water (100 mL). The organic layer of the filtrate was washed with $NaHCO_3$ (100 mL) and brine (50 mL), dried over anhydrous sodium sulfate, filtered and the solvent removed under reduced pressure to provide a colorless solid which was purified by silica gel chromatography (50% ethyl acetate/hexanes) to give hexa-O-acetyl-lactal (1.01 g, 61%).

EXAMPLE 7

This example describes the synthesis of penta-O-acetyl-O-((o-methoxy)benzoyl)-lactal. Hexa-O-acetyl-lactal (1.00 g) was dissolved with o-anisic acid (0.326 g, 1.2 equiv) and iodine (0.090 g, 0.20 equiv) in 45 mL of THF and quickly cooled to −78° C. A 1 mm Hg vacuum line was then attached and the reaction mixture allowed to warm slowly to −5° C. This reaction mixture was stirred for 3 h under these conditions, replacing the lost THF solvent periodically. The reaction mixture was then poured onto 50 mL ethyl acetate and washed successively with saturated aqueous $Na_2S_2O_3$, saturated aqueous $NaHCO_3$, and brine. The organic layer was dried over anhydrous sodium sulfate, filtered, and the solvent removed under reduced pressure. The resultant crude oil was purified by silica gel chromatography (75% ethyl acetate in hexanes) to provide penta-O-acetyl-O-((o-methoxy)benzoyl)-lactal (1.00 g, 86%) as an inseparable mixture of 4 isomers.

EXAMPLE 8

This example describes the synthesis of hexa-O-(chloroacetyl)-maltal. Hexa-O-acetyl-maltal (4.50 g) was dissolved in 70 mL of methanol and 0.400 g of sodium methoxide was added. The solution was stirred at room temperature overnight, whereupon the solvent was removed under reduced pressure. Silica gel chromatography (25% methanol in ethyl acetate) provided 2.20 g of a syrup which was immediately dissolved in a mixture of 25 mL of DMF, 25 mL of THF and 5.64 g of pyridine. The reaction mixture was cooled to 0°, 8.06 g of chloroacetyl chloride was added, and the reaction mixture was allowed to warm to room temperature and was stirred for 3 hours. The mixture was poured onto 350 mL of $CH_2Cl_2$, the resultant mixture was washed successively with 500 mL of water (2×), 200 mL of saturated aqueous $CuSO_4$, 200 mL of saturated aqueous $NaHCO_3$, and 200 mL of brine. The organic layer was dried over anhydrous sodium sulfate, filtered, and concentrated under reduced pressure. The crude solid was purified by silica gel chromatography (30% ethyl acetate in hexanes) to provide 3.22 g (52% from hexa-O-acetyl-maltal) of hexa-O-(chloroacetyl)-maltal as a light yellow solid.

$[\alpha]_D^{20}$ +43.4° (c=1.05, $CHCl_3$); $^1H$ NMR (360 MHz, $CDCl_3$) δ 4.00 (s, 2H), 4.00–4.15 (m, 2H), 4.05 (s, 2H), 4.07 (s, 4H), 4.15 (s, 4H), 4.27–4.53 (m, 5H), 4.91 (dd, J=5.4, 4.4 Hz, 1H), 4.95 (dd, J=10.1, 3.9 Hz, 1H), 5.14 (dd, J=10.1, 9.7 Hz, 1H), 5.24 (br s, 1H), 5.50 (d, J=4.3 Hz, 1H), 5.53 (dd, J=10.8, 9.7 Hz, 1H), 6.52 (d, J=5.7 Hz, 1H); $^{13}C$ NMR (90 MHz, $CDCl_3$) δ 40.25 (t, 2C), 40.29 (t), 40.58 (t), 40.63 (t), 40.71 (t), 62.86 (t), 63.06 (t), 68.01 (d), 69.20 (d), 69.43 (d), 70.85 (d), 71.42 (d), 73.09 (d), 73.45 (d), 95.77 (d), 97.40 (d), 146.23 (d), 166.40 (s), 166.68 (s), 166.73 (s), 166.48 (s), 166.98 (s, 2C); IR (KBr) 569 (w), 703 (w), 763 (w), 792 (m), 927 (m), 959 (m), 1009 (m), 1046 (s), 1167 (s), 1249 (m), 1287 (m), 1313 (m), 1410 (m), 1649 (w), 1761 (s), 2961 (w) $cm^{-1}$.

EXAMPLE 9

This example describes the synthesis of hexa-O-(chloroacetyl)-lactal. Hexa-O-acetyl-lactal (4.00 g) was dissolved in 70 mL of methanol and 0.400 g of sodium methoxide was added. The solution was stirred at room temperature for 2 days, during which time a white solid appeared. The reaction mixture was cooled to 0°, filtered through a sintered glass funnel, and washed with 5 mL ice-cold methanol The white solid (1.49 g, 67%) was dried under reduced pressure and 0.900 g was dissolved in 2.00 g of pyridine and 25 mL of DMF. The reaction mixture was cooled to 0°, whereupon 2.40 g of chloroacetyl chloride was added. The reaction mixture was allowed to warm to room temperature and was stirred overnight. The mixture was poured onto 100 mL of $CH_2Cl_2$, and the resultant mixture was washed successively with 100 mL of water (2×), 50 mL of saturated aqueous $CuSO_4$, 50 mL of saturated aqueous $NaHCO_3$, and 50 mL of brine. The organic layer was dried over anhydrous sodium sulfate, filtered, and concentrated under reduced pressure. The crude solid was purified by silica gel chromatography (30% ethyl acetate in hexanes) to provide 1.41 g (42% from hexa-O-acetyl-lactal) hexa-O-(chloroacetyl)-lactal as a light yellow solid.

mp 56–58° C.; $[\alpha]_D^{20}$ −12.7° (c=1.03, $CHCl_3$); $^1H$ NMR (360 MHz, $CDCl_3$) δ 3.99 (s, 2H), 4.04–4.20 (m, 1H), 4.08 (s, 2H), 4.11 (s, 2H), 4.12 (s, 2H), 4.14 (s, 2H), 4.20 (s, 2H), 4.21–4.38 (m, 5H), 4.54 (dd, J=12.0, 3.2 Hz, 1H), 4.83 (d, J=7.6 Hz, 1H), 4.87 (dd, J=6.2, 3.6 Hz, 1H), 5.19 (1H) and 5.25 (1H) (ABq, $J_{AB}$=10.5 Hz; the 5.19 and 5.25 are further split into d with J=3.2 Hz and 7.6 Hz, respectively), 5.47 (d, J=2.4 Hz, 1H), 5.52 (dd, J=4.3,4.1 Hz, 1H), 6.47 (d, J=6.2 Hz, 1H); $^{13}$C NMR (90 MHz, CDCl$_3$) δ 40.23 (t), 40.39 (t, 2C), 40.50 (t), 40.67 (t), 40.87 (t), 62.33 (t), 62.33 (t) 62.81 (t), 68.51 (d), 69.83 (d), 70.07 (d), 70.46 (d), 71.88 (d), 73.81 (d), 73.90 (d), 97.90 (d), 100.17 (d), 146.22 (d), 165.96 (s), 166.50 (s), 166.56 (s), 166.84 (s), 167.01 (s), 167.20 (s); IR (KBr) 791 (w), 926 (w), 958 (w), 1037 (m), 1075 (m), 1165 (s), 1247 (m), 1286 (m), 1315 (m), 1410 (m), 1651 (w), 1759 (s), 2960 (w) cm$^{-1}$.

EXAMPLE 10

This example describes the synthesis of tri-O-(methoxyacetyl)-glucal. Tri-O-acetyl-glucal (13.5 g) was dissolved in 100 mL of methanol and ammonia was bubbled through the solution until 5.60 g dissolved. The reaction mixture was stirred overnight whereupon the solvent was removed under reduced pressure. The resultant oil was then triturated with 100 mL of a 5:1 CHCl$_3$:hexanes solution. The solid thus obtained was dissolved in 100 ml of THF and the solution was treated with dicyclohexylcarbodiimide (35.00 g), 4-(dimethylamino)pyridine (0.500 g), and methoxyacetic acid (15.0 g). The reaction mixture was stirred overnight and filtered. After dilution with 300 mL of ether, the solution was washed first with 300 mL of saturated aqueous NaHCO$_3$ and then with 300 mL of brine, dried over anhydrous sodium sulfate, filtered, and the solvent removed under reduced pressure. Silica gel chromatography (30% ethyl acetate in hexanes) of the crude product provided 6.33 g (35%) of tri-O-(methoxyacetyl)-glucal as a colorless oil.

$[\alpha]_D^{20}$ −1.1° (c=1.20, CHCl$_3$); $^1$H NMR (300 MHz, CDCl$_3$) δ 3.43 (s, 3H), 3.43 (s, 3H), 3.45 (s, 3H), 4.02 (s, 2H), 4.06 (s, 2H), 4.09 (s, 2H), 4.26–4.33 (m, 2H), 4.53 (dd, J=6.6, 5.6 Hz, 1H), 4.86 (dd, J=6.1, 3.1 Hz, 1H), 5.33 (dd, J=8.3, 6.1 Hz, 1H), 5.52 (m, 1H), 6.49 (dd, J=6.1, 1.3 Hz, 1H); $^{13}$C NMR (76 MHz, CDCl$_3$) δ 59.33 (q, 3C), 61.33 (t), 67.48 (d), 68.12 (d), 69.45 (t, 2C), 69.61 (t), 73.73 (d), 98.71 (d), 145.95 (d), 168.99 (s), 169.65 (s), 169.71 (s); IR (neat) 720, 754, 825, 933, 969, 1024, 1065, 1128 (s), 1190 (s), 1246 (m), 1407 (w), 1422 (w), 1452 (m), 1650 (m), 1760 (s), 2829 (m), 2936 (m) cm$^{-1}$.

EXAMPLE 11

This example describes the synthesis of hexa-O-(methoxyacetyl)-maltal. Hexa-O-acetyl-maltal (20.0 g) was dissolved in 100 mL of methanol and ammonia was bubbled through the solution until 9.80 g dissolved. The reaction mixture was stirred overnight whereupon the solvent was removed under reduced pressure. The resultant oil was triturated three times with 80 mL of CHCl$_3$. The solid thus obtained was dissolved in 200 mL of THF and the solution was treated with dicyclohexylcarbodiimide (45.0 g), 4-(dimethylamino)pyridine (0.500 g), and methoxyacetic acid (20.0 g). The reaction mixture was stirred overnight, filtered, and diluted with 300 mL of ether. The resulting mixture was washed first with 300 mL of saturated aqueous NaHCO$_3$ and then with 300 mL of brine, dried over anhydrous sodium sulfate, filtered, and the solvent removed under reduced pressure. Silica gel chromatography (75% ethyl acetate in hexanes) of the crude product provided 7.22 g of hexa-O-(methoxyacetyl)-maltal (30%) as a colorless oil.

$[\alpha]_D^{20}$ +50.7° (c=1.08, CHCl$_3$); $^1$H NMR (300 MHz, CDCl$_3$) δ 3.38 (s, 3H), 3.39 (s, 3H), 3.41 (s, 3H), 3.43 (s, 3H), 3.44 (s, 3H), 3.45 (s, 3H), 3.94 (s, 2H), 3.99 (s, 4H), 4.01 (d, J=2.2 Hz, 2H), 4.09 (s, 4H), 3.97–4.14 (m, 2H), 4.23 (1H) and 4.31 (1H) (ABq, $J_{AB}$=12.5 Hz, the 4.23 and the 4.31 peaks are further split into d, J=2.2 and 4.0 Hz, respectively), 4.36–4.46 (m, 3H), 4.88 (dd, J=6.1, 3.3 Hz, 1H), 4.95 (dd, J=10.2, 4.0 Hz, 1H), 5.14 (dd, J=10.2, 9.5 Hz, 1H), 5.21 (dd, J=4.1, 4.1 Hz), 5.45 (dd, J=4.1 Hz, 1H), 5.48 (dd, J=9.5, 9.5 Hz, 1H), 6.46 (dd, J=6.2, 1.1 Hz); $^{13}$C NMR (90 MHz, CDCl$_3$) δ 59.34 (q, 2C), 59.42 (q, 4C), 61.59 (t), 61.71 (t), 68.07 (d), 68.22 (d), 68.43 (d), 69.27 (t, 2C), 69.31 (t), 69.43 (t), 69.57 (t), 69.72 (t), 70.11 (d), 70.36 (d), 72.95 (d), 73.77 (d), 95.95 (d), 97.93 (d), 145.93 (d), 169.19 (s), 169.51 (s), 169.67 (s), 169.77 (s), 169.89 (s), 169.96 (s); IR (neat) 722 (w), 932 (m), 1045 (s), 1125 (s), 1183 (s), 1246 (s), 1375 (m), 1421 (m), 1452 (m), 1650 (m), 1762 (s), 2829 (m), 1935 (m), 2829 (m), 2935 (m) cm$^{-1}$.

EXAMPLE 12

This example describes the synthesis of fusidic acid [3α,11α,16β-Trihydroxy-29-nor-8α,9β,13α,14β-dammara-17(20),24-dien-21-oic acid 16-acetate]. Four Fusidin 1-gram tablets (obtained from Leo Laboratories Limited, Dublin, Ireland), each containing 250 mg of sodium fusidate (1.96 mmol), were crushed in a mortar. The white powder was dissolved in water (100 mL) and the solution was acidified with 10% aqueous hydrochloric acid to make the pH of the solution 2–3. The aqueous layer was extracted with chloroform (3×100 mL). The combined organic layers were dried over anhydrous magnesium sulfate and the solvent was removed under reduced pressure, providing fusidic acid as a white powder (940 mg, 98% recovery). Spectroscopic data were identical with those reported. [See Riisom et al., Tetra. Letts. 2247 (1974)].

II. Synthesis of Novel Analogs

EXAMPLE 13

This example describes the synthesis of fusidic acid 3-(4,6-di-O-acetyl-2,3-dideoxy-α-D-erythro-hex-2-enopyranoside) [FSA-G-1]. To a solution of fusidic acid (1.03 g, 1.99 mmol) and tri-O-acetyl-glucal (0.701 g, 2.57 mmol) in dry tetrahydrofuran (30 mL) was added iodine (139 mg, 20 mol %) at room temperature under nitrogen atmosphere. The mixture was stirred for 2.5 hr, whereupon the reaction mixture was diluted with diethyl ether (45 mL). The resulting mixture was washed with 0.1 M aqueous Na$_2$S$_2$O$_3$ (30 mL) and 10% aqueous NaHCO$_3$ (30 mL). The organic layer was dried over anhydrous magnesium sulfate and the solvent was removed under reduced pressure. The resulting oily residue was purified by silica gel flash chromatography using dichloromethane/ethyl acetate/methanol (5/1/0 to 3/3/1) as the eluent, providing FSA-G-1 (>20:1 α/β-anomers) as a white powder (1.04 g, 72%): mp 111–112°; TLC R$_f$ 0.60 (9/1 dichloromethane/methanol); $[\alpha]_D^{21}$−1.5° (c=0.2, CHCl$_3$); $_1$H NMR of the α-anomer (360 MHz, CDCl$_3$) δ 0.87 (d, 3H, J=6.6 Hz, 30-CH$_3$), 0.91 (s, 3H, 19-CH$_3$), 0.97 (s, 3H, 18-CH$_3$), 1.36 (s, 3H, 32-CH$_3$), 1.59 (s, 3H, 26-CH$_3$), 1.68 (s, 3H, 27-CH$_3$), 1.96 (s, 3H, 16-OAc), 2.09 (s, 3H, 16-OAc) 2.11 (s, 3H, 16-OAc), 3.05 (brd, 1H, J=10.8 Hz, 13-H), 3.66 (m, 1H, 3-H), 4.16 (m, 3H, 5'-, 6'-, 6"-H), 4.30–4.36 (m, 1H, 11-H), 5.04 (s, 1H, 1'-H), 5.10 (dd, 1H, J=7.1, 7.1 Hz, 24-H), 5.28 (d, 1H, J=9.6 Hz, 4'-H), 5.82 (br d, 1H, J=11.1 Hz, 2'-H), 5.89 (d, 1H, J=8.2 Hz, 16-H); $^{13}$C NMR of the α-anomer (90.6 MHz, CDCl$_3$) δ 15.74, 17.66, 17.88, 20.51, 20.73, 20.94, 22.71, 24.08, 25.61, 28.28, 28.63, 28.85, 31.09, 32.28, 35.42, 36.27, 36.76, 36.86, 38.85, 39.26, 44.22, 48.60, 49.07, 63.23, 65.50, 66.67, 67.66, 68.17, 74.30, 81.07, 96.56, 128.13, 128.21, 129.45, 132.53, 151.04, 170.28, 170.47, 170.80, 174.56; IR (KBr) 3539–3507 (br), 2954 (s), 1744 (s), 1698 (s), 1374 (s), 1238 (s), 1037 (s), 755 (s) cm$^{-1}$. Anal. Calcd for $C_{41}H_{60}O_{11}$ .1/2 $CHCl_3$: C, 63.21; H, 7.73. Found: C, 63.17; H, 7.49.

EXAMPLE 14

This example describes the synthesis of fusidic acid 3-(2,3-dideoxy-α-D-erythro-hex-2-enopyranoside) [FSA-G-2]. To a solution of FSA-G-1 (364 mg, 0.57 mmol) in methanol (10 mL) was added 0.1 M aqueous $Ba(OH)_2$ (9 mL) at room temperature. The mixture was stirred for 3 hr, whereupon the solution was extracted with 4/1 chloroform/ 1-butanol (3×50 mL). The combined organic layers were dried over anhydrous magnesium sulfate and concentrated under reduced pressure. The crude residue thus obtained was purified by silica gel flash chromatography using a chloroform to ethyl acetate gradient as the eluent, providing FSA-G-2 (>100:1 α/β-anomers) as a white powder (165 mg, 45%): mp 129–131°; TLC $R_f$ 0.20 (9/1 dichloromethane/methanol); $[\alpha]_D^{21}$ –29.2° (c=2.01,$CHCl_3$); $^1$H NMR (360 MHz, $CDCl_3$) δ 0.87 (d, 3H, J=6.0 Hz, 30-$CH_3$), 0.89 (s, 3H, 19-$CH_3$), 0.97 (s, 3H, 18-$CH_3$), 1.33 (s, 3H, 32-$CH_3$), 1.59 (s, 3H, 26-$CH_3$), 1.67 (s, 3H, 27-$CH_3$), 1.97 (s, 3H, 16-OAc), 3.01 (br s, 1H, 13-H), 3.56–3.62 (br s, 1H, 3-H), 3.78–3.88 (m, 3H, 5'-, 6'-, 6"-H), 4.09 (br s, 1H, 4'-H), 4.31 (br s, 1H, 11-H), 4.97 (s, 1H, 1'-H), 4.97 (br s 1H, 24-H), 5.73 and 5.93 ($AB_q$,2H,$J_{AB}$=10.0 Hz, 2'-H and 3'-H, respectively), 5.85 (br s, 1H, 16-H); $^{13}$C-NMR (90.6 MHz, $CDCl_3$) δ 15.74, 17.70 (2×C), 20.57, 20.79, 23.20, 23.69, 25.64, 28.48, 28.79, 30.74, 31.84, 35.40, 36.49 (2×C), 36.60, 38.83, 39.33, 44.20, 48.55, 49.23, 62.74, 64.38, 68.03, 71.70, 74.48, 77.20, 81.20, 96.42, 123.11, 126.46, 129.69, 132.39, 132.88, 150.21, 170.97, 174.03; IR (KBr) 3496–3395 (br), 2968–2867 (br), 1721–1713 (br s), 1376 (s), 1264 (s), 1027 (s), 753 (s) cm$^{-1}$. Anal. Calcd for $C_{37}H_{56}O_9$1/2 $CHCl_3$: C, 63.95; H, 8.08. Found: C, 63.68; H, 7.97.

EXAMPLE 15

This example describes the oxidation of FSA-G-1 to give 11-dehydrofusidic acid 3-(4,6-di-O-acetyl-2,3-dideoxy-α-D-erythro-hex-2-enopyranoside) [FSA-G-3]. To a solution of FSA-G-1 (144 mg, 0.57 mmol) in dry dichloromethane (10 mL) was added 12-I-5 triacetoxyperiodinane [the Dess Martin reagent; see Dess and Martin, J. Org. Chem. 48:4155 (1983)] (150 mg, 0.36 mmol) at room temperature. The reaction mixture was stirred for 3.5 hr, whereupon the mixture was diluted with diethyl ether (20 mL). The organic mixture was washed successively with 10% aqueous $NaHCO_3$ (15 mL), 0.1 M aqueous $Na_2S_2O_3$ (15 mL), and brine (15 mL). The organic layer was dried over anhydrous magnesium sulfate, and the solvent was removed under reduced pressure to obtain FSA-G-3 as an anomerically pure, white powder (144 mg, 80%): mp 115–116°; TLC $R_f$ 0.60 (9/1 dichloromethane/methanol); $[\alpha]_D^{21}$+31.2° (c=1.44,$CHCl_3$); $^1$H NMR (360 MHz, $CDCl_3$) δ 0.85 (d, 3H, J=6.3 Hz, 30-$CH_3$), 1.02 (s, 3H, 19-$CH_3$), 1.15 (s, 3H, 18-$CH_3$), 1.17 (s, 3H, 32-$CH_3$), 1.59 (s, 3H, 26-$CH_3$), 1.67 (s, 3H, 27-$CH_3$), 1.99 (s, 3H, 16-OAc), 2.09 (s, 3H, OAc), 2.10 (s, 3H, OAc), 3.63 (br s, 1H, 3-H), 4.15–4.23 (m, 3H, 5'-, 6'-, 6"-H), 5.04 (br s, 1H, 1'-H), 5.08 (br s 1H, 24-H), 5.26 (d, 1H, J=9.3 Hz, 4'-H), 5.84 (br s, 2H, 2'-H and 3'-H), 5.95 (d, 1H, J=8.6 Hz, 16-H); $^{13}$C-NMR of the (90.6 MHz, $CDCl_3$) δ 15.94, 17.06, 17.69, 20.21, 20.48, 20.78, 20.99, 21.29, 22.89, 25.63, 27.98, 28.67, 28.82, 29.01, 32.38, 34.98, 37.42, 38.08, 39.01, 41.08, 44.78, 47.67, 48.66, 58.53, 63.22, 65.47, 66.95, 74.23, 81.56, 96.62, 122.50, 128.20, 130.52, 133.85, 148.77, 170.36 (2×C), 170.90, 174.12, 210.19; IR (KBr) 3540–3360 (br w), 2954 (br s), 2876 (s), 1744 (s), 1373 (w), 1236 (s), 1103 (w), 1037 (s) cm$^{-1}$.

EXAMPLE 16

This example describes the hydrolysis of FSA-G-3 to give 11-dehydrofusidic acid 3-(2,3-dideoxy-α-D-erythro-hex-2-enopyranoside) [FSA-G-4]. To a solution of FSA-G-3 (80 mg, 0.11 mmol) in methanol (10 mL) was added 0.1 M aqueous $Ba(OH)_2$ (4 mL) at room temperature. The mixture was stirred for 3 hr, whereupon the solution was extracted with 4/1 chloroform/1-butanol (3×15 mL). The combined organic layers were dried over anhydrous magnesium sulfate and concentrated under reduced pressure. The crude residue thus obtained was purified by silica gel flash chromatography using a chloroform to ethyl acetate gradient as the eluent, providing FSA-G-4 (10:1 α/β-anomers) as a white powder (39 mg, 55%): mp 106°; TLC $R_f$ 0.22 (9/1 dichloromethane/methanol); $[\alpha]_D^{21}$+13.3° (c=0.57,$CHCl_3$); $^1$H NMR (360 MHz, $CDCl_3$) δ 0.85 (d, 3H, J=6.5 Hz, 30-$CH_3$), 1.00 (s, 3H, 19-$CH_3$), 1.12 (s, 3H, 18-$CH_3$), 1.17 (s, 3H, 32-$CH_3$), 1.59 (s, 3H, 26-$CH_3$), 1.66 (s, 3H, 27-$CH_3$), 2.00 (s, 3H, 16-OAc), 3.60 (s, 1H, 3-H), 3.75–3.92 (m, 3H, 5'-, 6'-, 6"-H), 4.24 (d, 1H, J=8.9 Hz, 4'-H), 4.98 (s, 1H, 1'-H), 5.08 (t, 1H, J=7.1 Hz, 24-H), 5.73 (br d, 1H, J=10.1 Hz, 3'-H), 5.90 (d, 1H, J=8.1 Hz, 16-H), and 5.93 (d, 1H, J=10.1 Hz, 2'-H)); $^{13}$C-NMR (90.6 MHz, $CDCl_3$) δ 15.92, 17.05, 17.72, 20.32, 20.54, 21.55, 22.51, 25.65, 28.04, 28.75, 28.99, 31.96, 35.28, 37.29, 38.08, 38.66, 41.34, 44.92, 47.96, 48.66, 58.54, 62.70, 64.42, 71.19, 74.30, 81.11, 96.45, 122.59, 126.63, 130.65, 132.50, 132.96, 147.61, 170.63, 173.38, 210.63; IR (KBr) 3459–3423 (br s), 2967–2877 (br s), 1714 (s), 1702 (s), 1036 (s), 753 (s) cm$^{-1}$.

EXAMPLE 17

This example describes the catalytic hydrogenation of FSA-G-1 to give 24,25-dihydrofusidic acid 3-(4,6-di-O-acetyl-2,3-dideoxy-α-D-erythro-hexanopyranoside) [FSA-G-5]. To a solution of FSA-G-1 (210 mg, 0.29 mmol) in absolute ethanol (10 mL) and dry benzene (30 mL) was added platinum oxide (2 spatula tips, 5 mol %) at room temperature. The air was removed by applying vacuum and flushing the mixture with nitrogen; this procedure was repeated three times. The flask was charged with hydrogen gas and the mixture was stirred for 2 hr, whereupon the hydrogen atmosphere was replaced with nitrogen. The platinum catalyst was removed by filtration, and the reaction mixture was concentrated under reduced pressure, providing FSA-G-5 (10:1 α/β-anomers) as a white solid (202 mg, 95%): mp 89–90°; TLC $R_f$ 0.60 (9/1 dichloromethane/methanol); $[\alpha]_D^{21}$+20.3° (c=0.69,$CHCl_3$); $^1$H NMR (360 MHz, $CDCl_3$) δ 0.85 (d, 3H, J=6.2 Hz, 30-$CH_3$), 0.87 (d, 6H, J=6.6 Hz, 26-$CH_3$ and 27-$CH_3$), 0.92 (s, 3H, 19-$CH_3$), 0.98 (s, 3H, 18-$CH_3$), 1.38 (s, 3H, 32-$CH_3$), 1.97 (s, 3H, 16-OAc), 2.06 (s, 3H, OAc), 2.08 (s, 3H, OAc), 3.06 (d, 1H, J=11.5 Hz, 13-H), 3.57 (br s, 1H, 3-H), 4.06–4.23 (m, 3H, 5'-, 6'-, 6"-H), 4.36 (br s, 1H, 11-H), 4.70 (td, 1H, J=10.0, 4.4 Hz, 4'-H), 4.85 (s, 1H, 1'-H), 5.89 (d, 1H, J=8.3 Hz, 16-H); $^{13}$C-NMR (90.6 MHz, $CDCl_3$) δ 16.18, 18.13, 20.63, 20.81, 20.96, 21.70, 21. 26, 22.70, 24.38, 27.79, 27.93, 28.77, 28.95, 29.40, 31.51, 32.96, 35.58, 36.33, 37.08, 37.28, 38.81, 39.08, 39.54, 44.07, 45.88, 48.87, 49.16, 63.74, 68.38, 68.49, 69.29, 74.45, 81.10, 98.97, 100.09, 131.09, 148.99, 170.32, 170.85, 171.14, 174.62; IR (KBr) 3578–3320 (br s), 2960–2944 (br s), 1738 (s), 1459 (s), 1251 (s), 1120 (s), 735 (w) cm⁻

EXAMPLE 18

This example describes the hydrolysis of FSA-G-5 to give 24,25-dihydrofusidic acid 3-(2,3-dideoxy-α-D-erythro-hexanopyranoside) [FSA-G-6]. To a solution of FSA-G-5 (30 mg, 0.04 mmol) in methanol (3 mL) was added 0.1 M aqueous Ba(OH)$_2$ (3 mL) at room temperature. The mixture was stirred for 3 hr, whereupon the hydrolyzed product was extracted with 4/1 chloroform/1-butanol (3×5 mL). The combined organic layers were dried over anhydrous magnesium sulfate and concentrated under reduced pressure. The crude solid was purified by silica gel flash chromatography using chloroform to ethyl acetate gradient as the eluent, providing an α/β (10:1) anomeric mixture of FSA-G-6 as a white powder (14 mg, 50%): mp 73–74°; TLC R$_f$ 0.20 (9/1 dichloromethane/methanol); [α]$_D^{21}$+27.1° (c=0.67,CHCl$_3$); $^1$H NMR (360 MHz, CDCl$_3$) δ 0.85 (d, 3H, J=5.7 Hz, 30-CH$_3$), 0.87 (d, 6H, J=6.6 Hz 26-CH$_3$ and 27-CH$_3$), 0.91 (s, 3H, 18-CH$_3$), 0.97 (s, 3H, 19-CH$_3$), 1.37 (s, 3H, 32-CH$_3$), 1.97 (s, 3H, 16-OAc), 3.03 (br d, 1H, J=12.7 Hz, 13-H), 3.53 (br s, 1H, 3-H), 3.74–3.84 (m, 3H, 5'-, 6'-, 6"-H), 4.34 (br s, 1H, 11-H), 4.79 (d, 1H, J=2.8 Hz, 1'-H), 5.87 (d, 1H, J=8.2 Hz, 16-H; $^{13}$C-NMR (90.6 MHz, CDCl$_3$) δ 16.04, 17.87, 20.68, 22.60 (2×C), 23.11, 27.84, 28.56, 28.91, 29.70, 29.94, 31.05, 32.21, 35.60, 36.60, 36.72 (2×C), 38.71, 38.98, 39.49, 44.15, 48.72, 49.23, 63.71, 68.21, 73.63, 74.42, 80.73, 83.73, 98.30, 131.10, 149.01, 170.94, 174.71; IR (KBr) 3472–3402 (br s), 2953–2932 (br s), 1717 (s), 1376 (s), 1261 (s), 1034 (s), 743 (w) cm⁻¹.

EXAMPLE 19

This example describes the oxidation of FSA-G-5 to give 11-dehydro-24,25-dihydrofusidic acid 3-(4,6-di-O-acetyl-2,3-dideoxy-α-D-erythro-hexanopyranoside) [FSA-G-7]. To a solution of FSA-G-5 (150 mg, 0.2 mmol) in dry dichloromethane (10 mL) was added the Dess Martin reagent (152 mg, 0.36 mmol) at room temperature under nitrogen atmosphere. The reaction mixture was stirred for 3.5 hr, whereupon the mixture was diluted with diethyl ether (20 mL). The organic mixture was washed successively with 10% aqueous NaHCO$_3$ (15 mL), 0.1 M aqueous Na$_2$S$_2$O$_3$ (15 mL), and brine (15 mL). The organic layer was dried over anhydrous magnesium sulfate and the solvent was removed under reduced pressure to obtain a 7:2 α/β anomeric mixture of FSA-G-7 as a white solid (140 mg, 95%): mp 95–97°; TLC R$_f$ 0.60 (9/1 dichloromethane/methanol); [α]$_D^{21}$+46.5° (c=3.0,CHCl$_3$); $^1$H NMR of the α anomer (360 MHz, CDCl$_3$) δ 0.85 (d, 3H, J=6.1 Hz, 30-CH$_3$), 0.86 (d, 6H, J=6.6 Hz, 26-, 27-CH$_3$), 1.99 (s, 3H, 16-OAc), 2.06 (s, 3H, OAc), 2.08 (s, 3H, OAc), 3.57 (br s, 1H, 3-H), 3.89 (d, 1H, J=10.0 Hz), 4.04–4.22 (m, 3H, 5'-, 6'-, 6"-H), 4.69–4.73 (m, 1H, 4'-H), 4.84 (s, 1H, 1'H), 5.92 (d, 1H, J=8.3 Hz, 16-H); $^{13}$C-NMR of the (90.6 MHz, CDCl$_3$) δ 16.15, 17.10, 20.47, 20.78, 21.09, 22.51 (2×C), 23.09, 24.27, 27.42, 27.80, 28.64, 29.13, 29.29, 30.71, 32.85, 34.88, 37.58, 38.14, 38.48, 38.94, 39.28, 41.04, 44.77, 47.32, 48.76, 58.64, 63.37, 68.16, 69.31, 74.23, 81.27, 98.90, 131.17, 147.50, 170.15, 170.30, 170.94, 174.39, 210.28; IR (KBr) 2958 (s), 2254 (s), 1735 (s), 1689 (s), 1375 (s), 1252 (s), 1037 (s), 903 (s), 735 (s) cm⁻¹.

EXAMPLE 20

This example describes the hydrolysis of FSA-G-7 to give 11-dehydro-24,25-dihydrofusidic acid 3-(2,3-dideoxy-α-D-erythro-hexanopyranoside) [FSA-G-8]. To a solution of FSA-G-7 (122 mg, 0.17 mmol) in methanol (4 mL) was added 0.1 M aqueous Ba(OH)$_2$ (6 mL) at room temperature. The mixture was stirred for 3 hr, whereupon the hydrolyzed product was extracted with 4/1 chloroform/1-butanol (3×5 mL). The combined organic layers were dried over anhydrous magnesium sulfate and concentrated under reduced pressure. The crude solid was purified by silica gel flash chromatography using chloroform to ethyl acetate gradient as the eluent, providing FSA-G-8 (>10:1 α/β anomers) as a white solid (60 mg, 55%): mp 71–73°; TLC R$_f$ 0.20 (9/1 dichloromethane/methanol); [α]$_D^{21}$+53.7° (c=1.8,CHCl$_3$); $^1$H NMR (360 MHz, CDCl$_3$) δ 0.85 (d, 3H, J=6.2 Hz, 30-CH$_3$), 0.86 (d, 6H, J=6.6 Hz, 26-, 27-CH$_3$), 1.02 (s, 3H), 1.17 (s, 6H), 2.00 (s, 3H, 16-OAc), 2.91 (br d, 1H, J=12.3 Hz, 13-H), 3.54 (br s, 1H, 3-H), 3.60–3.70 (m, 1H), 3.73–3.86 (m, 3H, 5'-, 6'-, 6"-H), 4.80 (s, 1H, 1'H), 5.91 (d, 1H, J=8.0 Hz, 16-H; $^{13}$C-NMR (90.6 MHz, CDCl$_3$) δ 16.16, 17.08, 20.26, 20.60, 21.38, 22.55 (2×C), 22.76, 27.47, 27.82, 28.74, 28.91, 29.07, 29.85, 32.38, 35.20, 37.42, 38.16, 38.54, 38.89, 41.27, 44.85, 47.60, 48.76, 58.64, 63.48, 67.96, 73.24, 74.21, 77.20, 80.93, 98.60, 131.32, 146.72, 170.48, 173.30, 210.56; IR (KBr) 3572 (br), 2927 (s), 1717 (s), 1596 (s), 1418 (s), 1121 (s), 616 (s) cm⁻¹.

EXAMPLE 21

This example describes the synthesis of fusidic acid 3-[4-O-(2,3,4,6-tetra-O-acetyl-α-D-glucopyranosyl)-6-O-acetyl-2,3-dideoxy-α-D-erythro-hex-2-enopyranoside] [FSA-M-1]. To a solution of fusidic acid (500 mg, 1.07 mmol) and hexa-O-acetyl-maltal (720 mg, 1.29 mmol) in dry tetrahydrofuran (35 mL) was added iodine (80 mg, 20 mol %) at room temperature under a nitrogen atmosphere. The mixture was stirred for 12 hr, whereupon the reaction mixture was diluted with chloroform (60 mL). The resulting mixture was washed with 0.1 M aqueous Na$_2$S$_2$O$_3$ (35 mL) and 10% aqueous NaHCO$_3$ (35 mL). The organic layer was dried over anhydrous magnesium sulfate and the solvent was removed under reduced pressure. The resulting oily residue was purified by silica gel flash chromatography using dichloromethane/ethyl acetate (1/0 to 0/1, v/v) as the eluent, providing FSA-M-1 (>100:1 α/β-anomers) as a light yellow powder (760 mg, 70%): mp 105–108°; TLC R$_f$ 0.55 (9/1 dichloromethane/methanol); [α]$_D^{21}$+32.1° (c=3.0,CHCl$_3$); $^1$H NMR (360 MHz, CDCl$_3$) δ 0.87 (d, 3H, J=6.4 Hz, 30-CH$_3$), 0.91 (s, 3H, 19-CH$_3$), 0.98 (s, 3H, 18-CH$_3$), 1.38 (s, 3H, 32-CH$_3$), 1.60 (s, 3H, 26-CH$_3$), 1.67 (s, 3H, 27-CH$_3$), 1.96 (s, 3H, 16-OAc), 2.01 (s, 3H, OAc), 2.03 (s, 3H, OAc), 2.09 (s, 3H, OAc), 2.10 (s, 3H, OAc), 2.11 (s, 3H, OAc), 3.08 (d, 3H, J=11.7 Hz, 13-H), 3.62 (br s, 1H, 3-H), 4.00–4.14 (m,3H), 4.24–4.35 (m, 4H), 4.83 (dd, 1H, J=10.3, 3.8 Hz), 5.00 (s, 1H, 1'H), 5.03–5.13 (m, 2H), 5.35 (d, 1H, J=3.8 Hz), 5.44 (t, 1H, J=9.9 Hz), 5.80 (m, 3H); $^{13}$C NMR (90.6 MHz, CDCl$_3$) δ 15.63, 17.57, 17.73, 20.40 (2×C), 20.48 (3×C), 20.65, 22.77, 23.92, 25.51, 28.26, 28.52, 28.79, 30.78, 32.14, 35.52, 36.34, 36.55, 36.60, 38.76, 39.19, 44.19, 48.50, 49.04, 61.61, 63.49, 66.89, 67.75 (2×C), 68.08, 69.66, 70.06, 70.76, 74.26, 77.18, 80.87, 93.21, 96.16, 122.93, 127.21, 128.84, 129.34, 132.31, 150.95, 169.41, 169.88, 170.36 (2×C), 170.47, 170.56, 174.72; IR (KBr) 3539–3499 (br s), 2938–2877 (br s), 1755 (s), 1749 (s), 1741 (s), 1735 (s), 1441 (s), 1373 (s), 1255 (s), 1225 (s), 1106 (s), 1039 (s), 754 (s) cm⁻¹.

EXAMPLE 22

This example describes the synthesis of fusidic acid 3-[4-O-(2,3,4,6-tetra-O-acetyl-β-D-galactopyranosyl)-6-O- acetyl-2,3-dideoxy-α-D-erythro-hex-2-enopyranoside] [FSA-L-1]. To a solution of fusidic acid (250 mg, 0.48 mmol) and hexa-O-acetyl-lactal (315 mg, 0.56 mmol) in dry tetrahydrofuran (20 mL) was added iodine (40 mg, 20 mol %) at room temperature under nitrogen atmosphere. The mixture was stirred for 24 hr, whereupon the reaction mixture was diluted with chloroform (30 mL). The resulting mixture was washed with 0.1 M aqueous $Na_2S_2O_3$ (20 mL) and 10% aqueous $NaHCO_3$ (20 mL). The organic layer was dried over anhydrous magnesium sulfate and the solvent was removed under reduced pressure. The resulting oily residue was purified by silica gel flash chromatography using dichloromethane/ethyl acetate (1/0 to 0/1, v/v) as the eluent, providing FSA-L-1 (>100:1 α/β-anomers) as a light yellow powder (317 mg, 65%): mp 73–74°; TLC $R_f$ 0.55 (9/1 dichloromethane/methanol); $[α]_D^{21}$+1.5° (c=1.0,$CHCl_3$); $^1H$ NMR (360 MHz, $CDCl_3$) δ 0.85 (d, 3H, J=6.6 Hz, 30-$CH_3$), 0.91 (s, 3H, 19-$CH_3$), 0.96 (s, 3H, 18-$CH_3$), 1.35 (s, 3H, 32-$CH_3$), 1.59 (s, 3H, 26-$CH_3$), 1.67 (s, 3H, 27-$CH_3$), 1.96 (s, 3H, 16-OAc), 1.98 (s, 3H, OAc), 2.05 (s, 3H, OAc), 2.09 (s, 3H, OAc), 2.16 (s, 3H, OAc), 3.06 (d, 3H, J=11.4 Hz, 13-H), 3.62 (br s, 1H, 3-H), 3.95 (t, 1H, J=6.8 Hz), 4.04–4.28 (m,6H), 4.31 (br s, 1H, 11-H), 4.60 (d, 1H, J=7.9 Hz), 5.00 (s, 1H, 1'H), 5.03 (d, 1H, J=3.3 Hz), 5.10 (t, 1H, J=6.9 Hz), 5.22 (dd, 1H, J=10.4, 7.9 Hz), 5.38 (d, 1H, J=3.1 Hz), 5.79 (dt, 1H, J=10.4, 2.2 Hz, 3'-H), 5.89 (d, 1H, J=8.3 Hz, 16-H), 6.06 (d, 1H, J=10.4 Hz, 2'-H); $^{13}C$ NMR (90.6 MHz, $CDCl_3$) δ 15.77, 17.71, 17.89, 20.60 (5×C), 20.80, 22.79, 24.12, 25.65, 28.33, 28.67, 28.93, 31.01, 32.37, 35.64, 36.40, 36.75, 38.89, 39.32, 44.25, 48.65, 49.10, 61.20, 63.36, 66.79, 67.20, 67.99, 68.82, 70.53, 70.81 (2×C), 73.81, 74.40, 77.20, 80.76, 96.45, 102.11, 122.99, 127.72, 129.48, 130.27, 131.42, 132.53, 151.08, 169.44, 170.08, 170.22, 170.45 (2×C), 170.78, 174.39; IR (KBr) 2955 (br), 1752 (s), 1371 (s), 1229 (s), 1040 (s), 754 (s) $cm^{-1}$.

EXAMPLE 23

This example describes the synthesis of fusidic acid 3-(4,6-bis-O-(chloroacetyl)-2,3-dideoxy-α-D-erythro-hex-2-enopyranoside) [FSA-ClAc-G-1]. To a solution of 345 mg of fusidic acid (0.66 mmol) and 300 mg of tri-O-(chloroacetyl)-glucal (0.80 mmol, 1.2 equiv) in 20 mL of dry THF was added 45 mg of iodine (0.17 mmol, 26 mol %) at room temperature under nitrogen atmosphere. The mixture was stirred for 4 days, whereupon the reaction mixture was diluted with 45 mL of diethyl ether. The resulting mixture was washed first with 30 mL of 0.1 M aqueous $Na_2S_2O_3$ and then with 30 mL of 10% aqueous $NaHCO_3$. The organic layer was dried over anhydrous sodium sulfate and the solvent was removed by rotary evaporation. The resulting oily residue was purified by silica gel flash column chromatography using a gradient elution with chloroform/ethyl acetate (1/0 to 0/1, v/v), providing FSA-ClAc-G-1 (20:1 α/β-anomers) as an off-white solid (200 mg, 38%): mp 88–89° C.; TLC $R_f$ 0.48 (9:1 dichloromethane/methanol); $[α]D^{22}$−2.5° (c=0.60,$CHCl_3$); $^1H$ NMR (360 MHz, $CDCl_3$) δ 0.87 (d,3H, J=6.6 Hz, 30-$CH_3$), 0.91 (s, 3H, 19-$CH_3$), 0.97 (s, 3H, 18-$CH_3$), 1.35 (s,3H, 32-$CH_3$, 1.60 (s, 3H 26-$CH_3$), 1.68 (s, 3H, 27-$CH_3$), 1.96 (s, 3H, 16-OAc), 3.04 (br d, 1H, J=9.0 Hz, 13-H), 3.60–3.66 (m or apparent diffused ddd, 1H, 3-H), 4.03–4.33 (m, 3H, 5'-, 6'-, 6"-H), 4.12 (s, 4H, 2×$CH_2Cl$), 4.35 (br s, 1H, 11-H 0, 5.05 (s, 1H, 1'-H), 5.10 (t, 1H, J=7.2 Hz, 24-H), 5.35 (dd, 1H, J=9.6, 1.2 Hz, 4'H), 5.84 (br d, 1H, J=11.1 Hz, 3'-H), 5.89 (br d, 1H, J=11.1 Hz, 2'-H), 5.90 (br d, 1H, J=9.3 Hz, 16-H); $^{13}C$ NMR (90.6 MHz, $CDCl_3$) δ 15.80, 17.71, 17.92, 20.53, 22.79, 24.07, 25.66, 28.34, 28.63, 28.96, 31.08, 32.36, 35.62, 36.31, 36.77, 36.86, 38.88, 39.30, 40.68 (2×C), 44.26, 48.63, 49.08, 64.71, 66.41, 67.26, 68.19, 77.02, 81.48, 96.49, 122.92, 127.13, 128.97, 129.51, 132.59, 151.21, 166.88, 167.17, 170.49, 174.99; IR (KBr) 3604–3310 (br), 2955 (br), 2875 (br), 1763 (s), 1739 (s), 1688 (s), 1445 (w), 1376 (s), 1253 (s), 1216 (w), 1167 (s), 1027 (s), 763 (m), 752 (m) $cm^{-1}$.

EXAMPLE 24

This example describes the hydrolysis of FSA-ClAc-G-1 to give FSA-G-2. A solution of FSA-ClAc-G-1 (110 mg, 0.14 mmol) in 2 mL of THF was diluted with a mixture of 3 mL of methanol and 1 mL of water. The solution was treated with 42 mg of $KHCO_3$ in 1 mL of water at room temperature and the resulting mixture was stirred for 3 hrs, whereupon the reaction mixture was extracted with chloroform (2×15 mL). The combined organic layers were dried over anhydrous magnesium sulfate and the solvent removed under reduced pressure. The resulting crude products were purified by silica gel flash column chromatography by following the same procedure as described for the preparation of FSA-G-2 at Example 14, providing 46 mg of FSA-G-2 (45%).

EXAMPLE 25

This example describes the glycosylation of fusidic acid with either hexa-O-(chloroacetyl)-maltal to give fusidic acid 3-[4-O-(2,3,4,6-tetra-O-(chloroacetyl)-α-D-glucopyranosyl)-6-O-(chloroacetyl)-2,3-dideoxy-α-D-erythro-hex-2-enopyranoside][FSA-ClAc-M-1] or hexa-O-(chloroacetyl)-lactal to give fusidic acid 3-[4-O-(2,3,4,6-tetra-O-(chloroacetyl)-β-D-galactopyranosyl)-6-O-(chloroacetyl)-2,3-dideoxy-α-D-erythro-hex-2-enopyranoside] [FSA-ClAc-L-1]. Fusidic acid will be dissolved in an appropriate amount of $CH_2Cl_2$ (~50 mL/gram) and 1.1 equivalents of hexa-O-(chloroacetyl)-maltal or hexa-O-(chloroacetyl)-lactal and 0.2 molar equivalents of a catalyst will be added.

If $I_2$ is chosen as the catalyst, then the reaction will be run at room temperature for at least one day. If no reaction is observed, then the reaction mixture will be heated to reflux. Other solvents, such as THF or acetone, could also be tried if the reaction proceeds slowly. Once the reaction is complete or reaches an apparent state of equilibrium, it will be worked up by standard procedures: dilution in an appropriate solvent (such as $CH_2Cl_2$ or ether); successive washings with 0.1 M aqueous $Na_2S_2O_3$, water, and brine; drying over anhydrous sodium sulfate; filtering; and removal of the solvent under reduced pressure. Silica gel chromatography using an appropriate solvent system (such as ethyl acetate/hexanes) will provide an acceptable yield of purified product.

If $BF_3$.etherate is chosen as a catalyst for the glycosylation reaction, the reaction mixture will first be cooled to −23° and then allowed to warm slowly to room temperature if needed. The reaction will proceed readily at room temperature or less. Once the reaction is complete or reaches an apparent state of equilibrium, it would be worked up by the standard procedures, and the product purified as outlined above.

EXAMPLE 26

This example describes the hydrolysis of FSA-ClAc-M-1 to give fusidic acid 3-[4-O-(α-D-glucopyranosyl)-2,3-dideoxy-α-D-erythro-hex-2-enopyranoside] [FSA-M-2] or the hydrolysis of FSA-ClAc-L-1 to give fusidic acid 3-[4-O-(β-D-galactopyranosyl)-2,3-dideoxy-α-D-erythro-hex-2- enopyranoside] [FSA-L-2]. After dissolving either of the two glycosides in methanol with a small amount of water, approximately 10 equivalents of $KHCO_3$ will be added and stirred at room temperature. After hydrolysis of the chloroacetate groups, the reaction mixture will be neutralized by using an ion exchange resin, although this step may not be necessary due to the acidic nature of the silica gel to be used in the purification. Subsequently, the solvent will be removed under reduced pressure, and silica gel purification with an appropriate solvent system (methanol in either ethyl acetate or a halogenated solvent such as chloroform or dichloromethane) should provide either FSA-M-2 or FSA-L-2 depending on the starting material employed.

EXAMPLE 27

This example describes the glycosylation of fusidic acid with the activated form of a glycal, i.e., di-O-acetyl-O-((o-methoxy)benzoyl)-glucal, penta-O-acetyl-O-((o-methoxy)benzoyl)-maltal, or penta-O-acetyl-O-((o-methoxy)benzoyl)-lactal. Fusidic acid will be dissolved in an appropriate solvent such as $CH_2Cl_2$ or THF and 1.1 equivalents of either di-O-acetyl-O-((o-methoxy)benzoyl)-glucal, penta-O-acetyl-O-((o-methoxy)benzoyl)-maltal, or penta-O-acetyl-O-((o-methoxy)benzoyl)-lactal and 0.2 molar equivalents of a catalyst such as $I_2$ will be added. The reaction will then be stirred at room temperature and monitored by TLC; the reaction will probably require much less time than their inactivated glycal counterparts. However, if necessary, the reaction mixture will be refluxed. Once the reaction is complete or has reached an apparent state of equilibrium, it will be worked up by standard procedures: dilution in an appropriate solvent (such as $CH_2Cl_2$ or ether); successive washings with 0.1 M aqueous $Na_2S_2O_3$, water, and brine; drying over anhydrous sodium sulfate; filtering; and removal of the solvent under reduced pressure should provide the crude product. Silica gel chromatography using a chloroform to ethyl acetate gradient should provide FSA-G-1, FSA-M-1, and FSA-L-1, respectively, depending on the activated glycal chosen.

EXAMPLE 28

Figure 17:
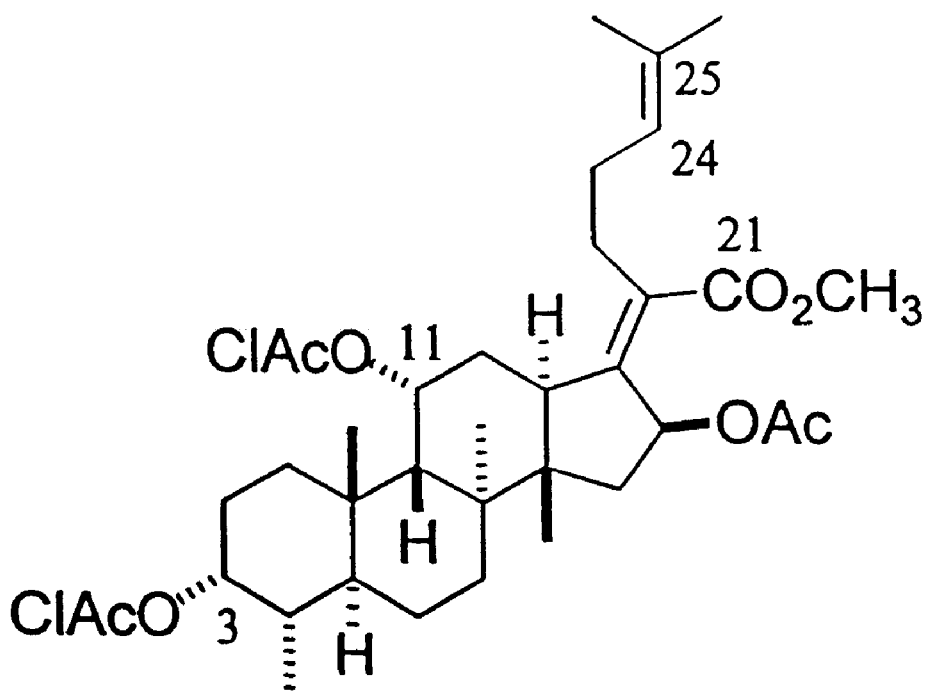
FIG. 17 shows the structure of a fusidic acid analog contemplated by the present invention that has protecting groups at positions C-3, C-11, and C-21.

This example describes the preparation of glycosylated analogs of fusidic acid that have a carbohydrate unit at C-24 of the aglycon. First, the hydroxyl groups at C-3 and C-11 and the carboxylic acid at C-21 will be protected. Fusidic acid will be dissolved in dry THF containing 3 equivalents of pyridine under a nitrogen atmosphere and the solution will be cooled to 0° C., whereupon 2.5 equivalents of monochloroacetyl chloride in THF will be added dropwise. The reaction mixture will be warmed to room temperature and will be stirred until the reaction is complete as indicated by TLC. The reaction mixture will be worked up using standard protocols. The crude reaction product may be used in the next step, or it may first need to be purified by silica gel chromatography. In either case, the material will be dissolved in dry dichloromethane under a nitrogen atmosphere and the resulting solution will be treated with 1.1 equivalents of a diazomethane precursor such as Diazold or N,N'-dimethyl-N, N'-dinitrosoterephthalamide which upon treatment with KOH produces diazomethane. The reaction will be stirred at room temperature until the TLC indicates that the reaction is complete. Workup following standard protocols and silica gel chromatography will give the molecule depicted in FIG. 17.

Second, the hydroxyl group will be introduced at C-24 by a hydroboration reaction. The molecule in FIG. 17 will be dissolved in dry THF under a nitrogen atmosphere and one equivalent of either (+)-Alpine borane or (−)-Alpine borane will be added. Alternatively, an achiral hydroboration reagent such as 9-borabicyclo[3.3.1]nonane [9-BBN] can be employed. The reaction will be achieved by heating if necessary. Oxidation of the resulting borane followed by standard workup procedures and silica gel chromatography will give the molecule in FIG. 18 having a hydroxyl group at C-24. Oxidation can be effected by either reacting the molecule with one equivalent of sodium hydroxide and an excess of 30% aqueous hydrogen peroxide while maintaining the reaction mixture at room temperature, or treating the borane with two equivalents of oxygen followed by 30% aqueous hydrogen peroxide. [For examples of the hydroboration and oxidation reactions, see Brown, "Organic Synthesis via Boranes" 61–62, 107–08, 110–12 (1975).] The particular C-24 epimer to be obtained (either R or S) will depend on the chirality of the Alpine borane reagent used.

Figure 18:
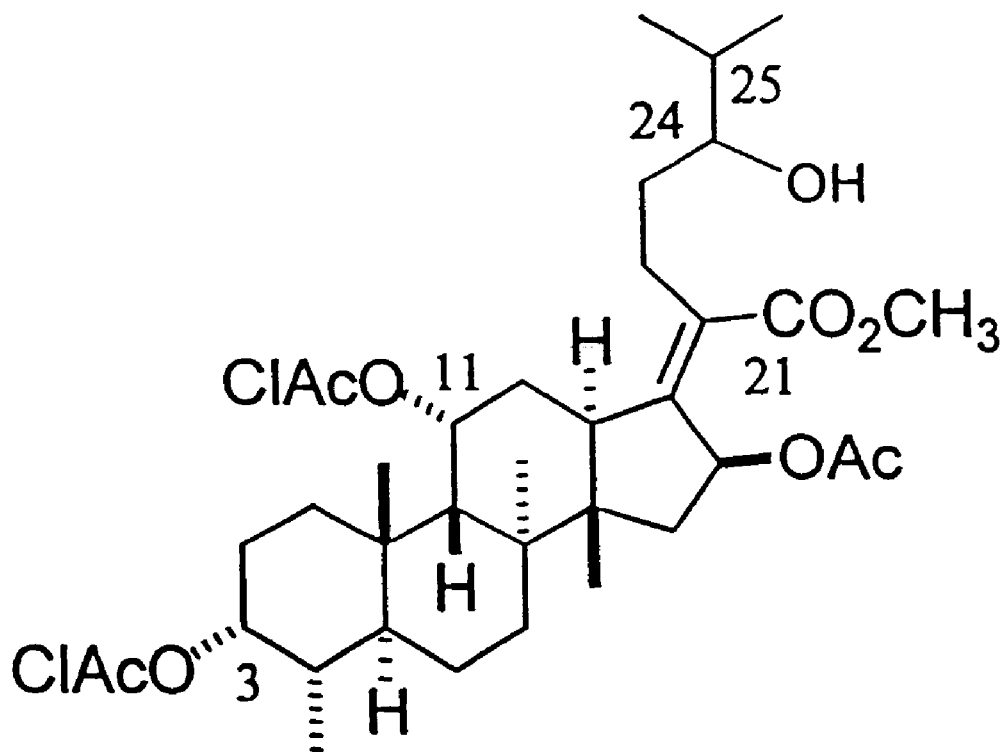
FIG. 18 shows the structure of a fusidic acid analog contemplated by the present invention that has protecting groups at positions C-3, C-11, and C-21 and an hydroxyl group at position C-24.
Figure 20:
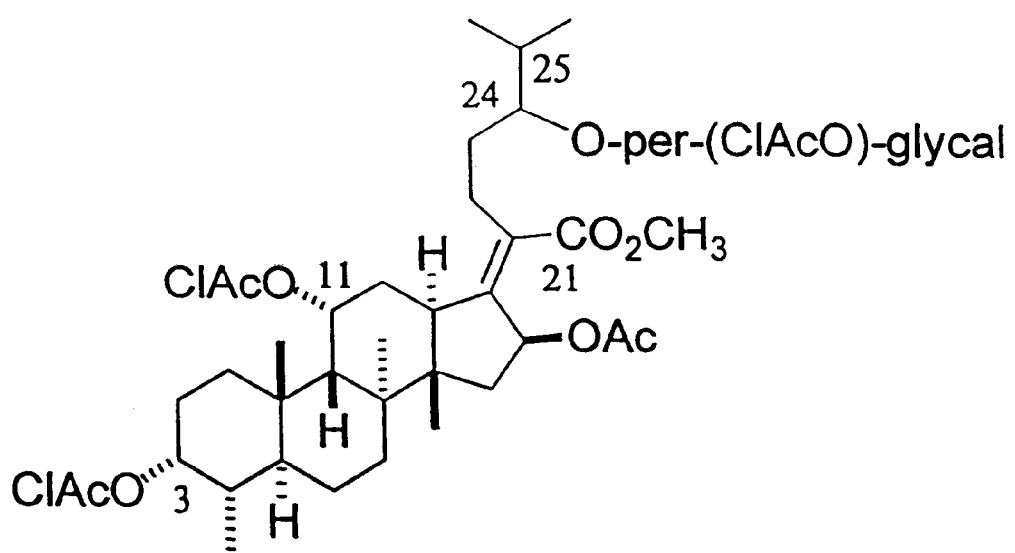
FIG. 20 shows the structure of a fusidic acid analog contemplated by the present invention that has protecting groups at positions C-3, C-11, and C-21 and at position C-24 a carbohydrate unit having protecting groups.
Figure 21:
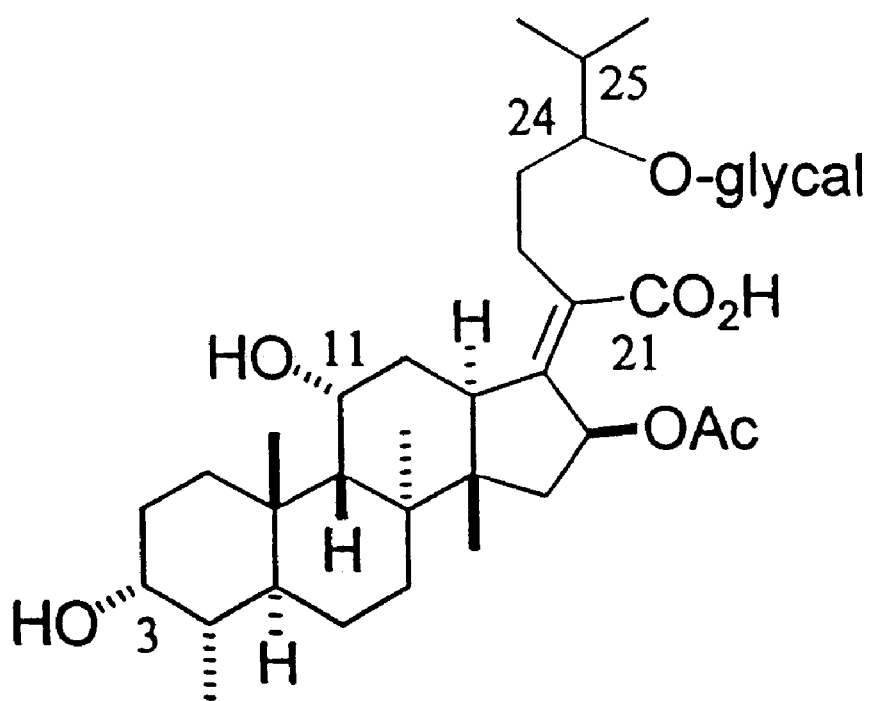
FIG. 21 shows the structure of a fusidic acid analog contemplated by the present invention that has a carbohydrate unit at position C-24.

The molecule in FIG. 18 will be glycosylated by following the standard procedure described in Examples 23 and 25 which employs the permonochloroacetylated glycals. Thus, a number of glycosylated fusidic acid derivatives such as that depicted in FIG. 20 will be prepared where the carbohydrate attached at the C-24 hydroxyl will be, for example, the permonochloroacetylated glucal, maltal, or lactal. The protecting groups of the glycosylated derivative can be hydrolyzed by following the procedure outlined in Experimentals 24 and 14 to hydrolyze the monochloroacetyls and methyl ester, respectively. These reactions will give the molecule shown in FIG. 21.

Figure 19:
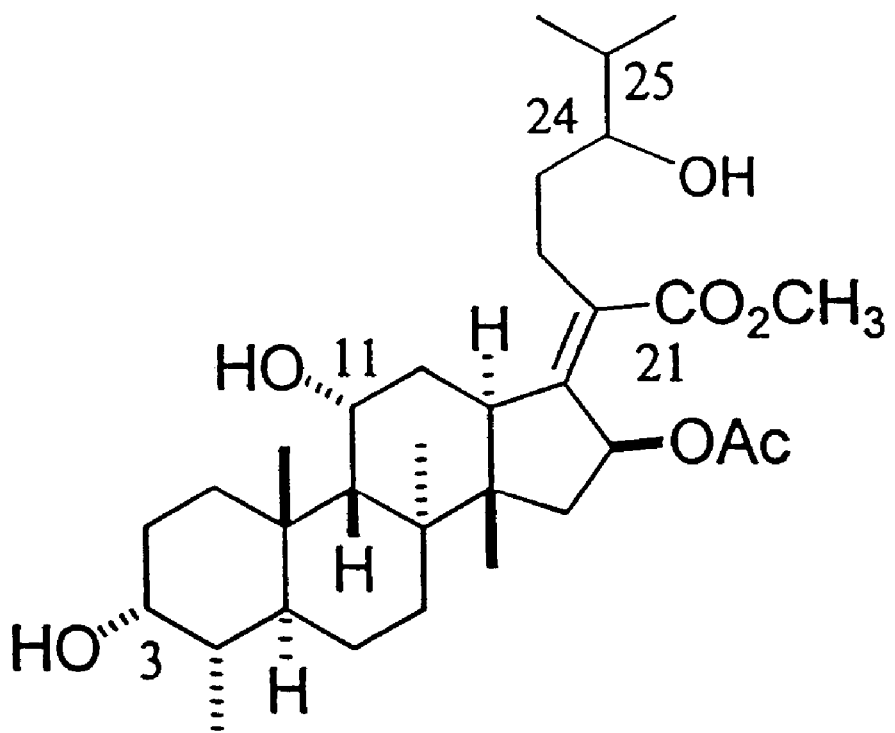
FIG. 19 shows the structure of a fusidic acid analog contemplated by the present invention that has a protecting group at position C-21 and an hydroxyl group at position C-24.
Figure 22:
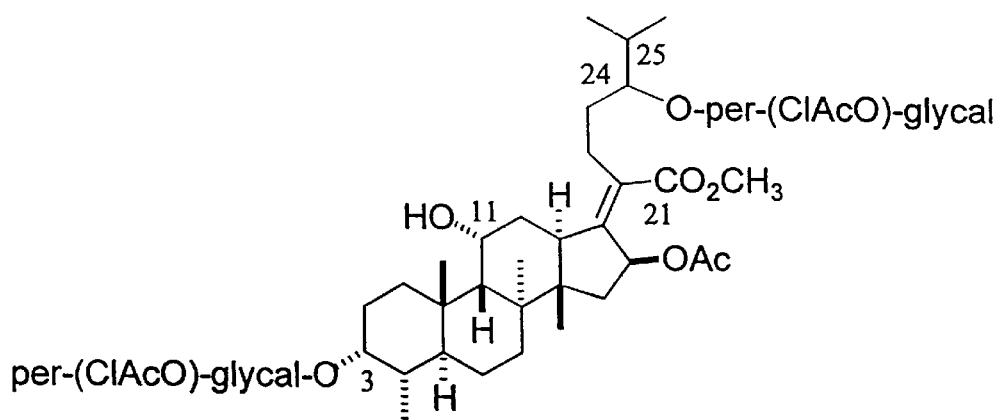
FIG. 22 shows the structure of a fusidic acid analog contemplated by the present invention that has a protecting group at position C-21 and at each of positions C-3 and C-24 a carbohydrate unit having protecting groups.
Figure 23:
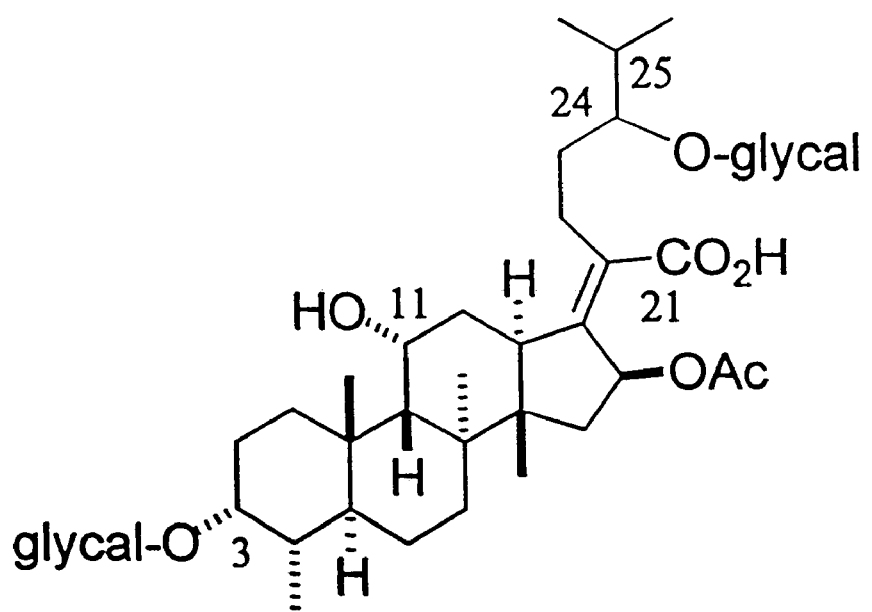
FIG. 23 shows the structure of a fusidic acid analog contemplated by the present invention that has a carbohydrate unit at each of positions C-3 and C-24.

Alternatively, the modified fusidic acid of FIG. 18 can first be deprotected by following the protocol in Experimental 24 to give the modified fusidic acid in FIG. 19 which has no protected hydroxyl groups yet still has a protected carboxylic acid at C-21. Reaction of this compound with 2.1 equivalents of a permonochloroacetylated glycal according to the protocol in Experimentals 23 and 25 will give the twice glycosylated analog of fusidic acid as shown in FIG. 22. The protecting groups can then be removed as discussed above by following Experimentals 24 and 14 to give the molecule depicted in FIG. 23.

EXAMPLE 29

This example describes the preparation of glycosylated analogs of fusidic acid that have a carbohydrate unit at C-25 of the aglycon. As in Example 27, the hydroxyl groups at C-3 and C-11 and the carboxylic acid at C-21 will be protected to give the molecule depicted in FIG. 17.

Second, the hydroxyl group will be introduced at C-25 by an oxymercuration-demercuration process. The molecule in FIG. 17 will be dissolved in aqueous THF and one equivalent of $Hg(ClO_4)_2$ will be added. If necessary, the reaction mixture will be warmed. Addition of 1.1 equivalents of $NaBH_4$ followed by standard workup and purification procedures will give the molecule depicted in FIG. 24.

Figure 24:
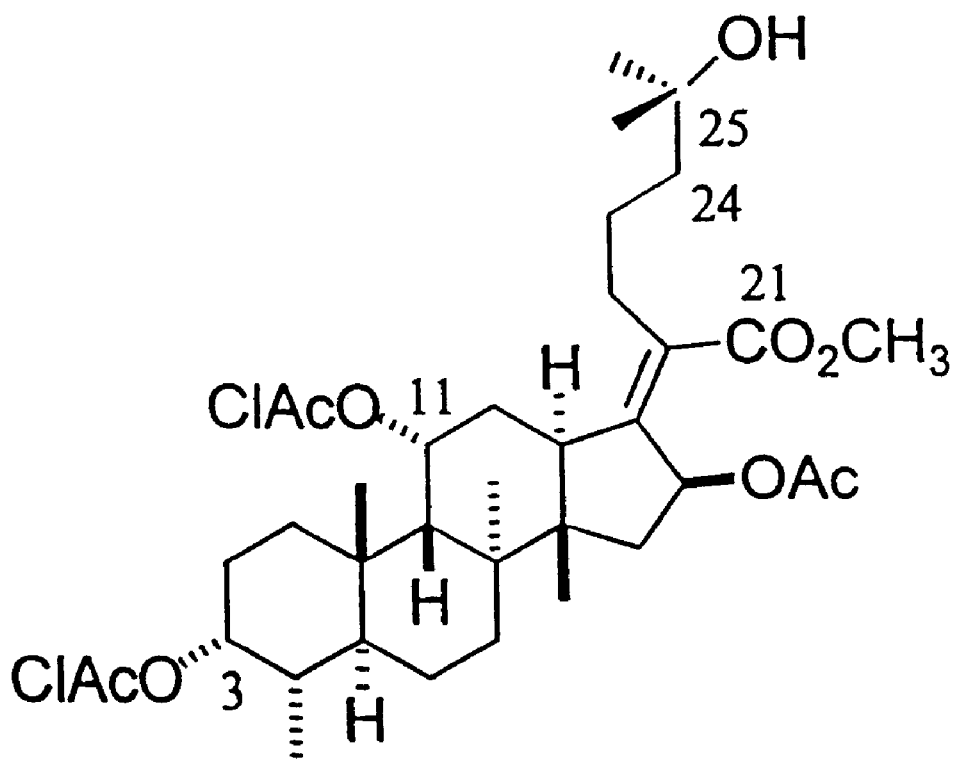
FIG. 24 shows the structure of a fusidic acid analog contemplated by the present invention that has protecting groups at positions C-3, C-11, and C-21 and an hydroxyl group at position C-25.
Figure 26:
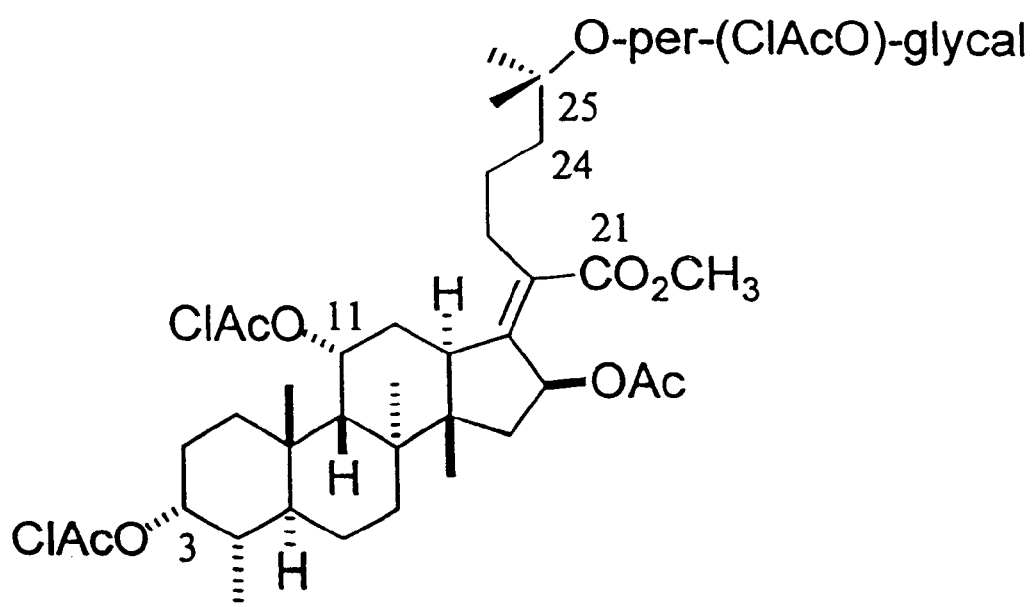
FIG. 26 shows the structure of a fusidic acid analog contemplated by the present invention that has protecting groups at positions C-3, C-11, and C-21 and at position C-25 a carbohydrate unit having protecting groups.
Figure 27:
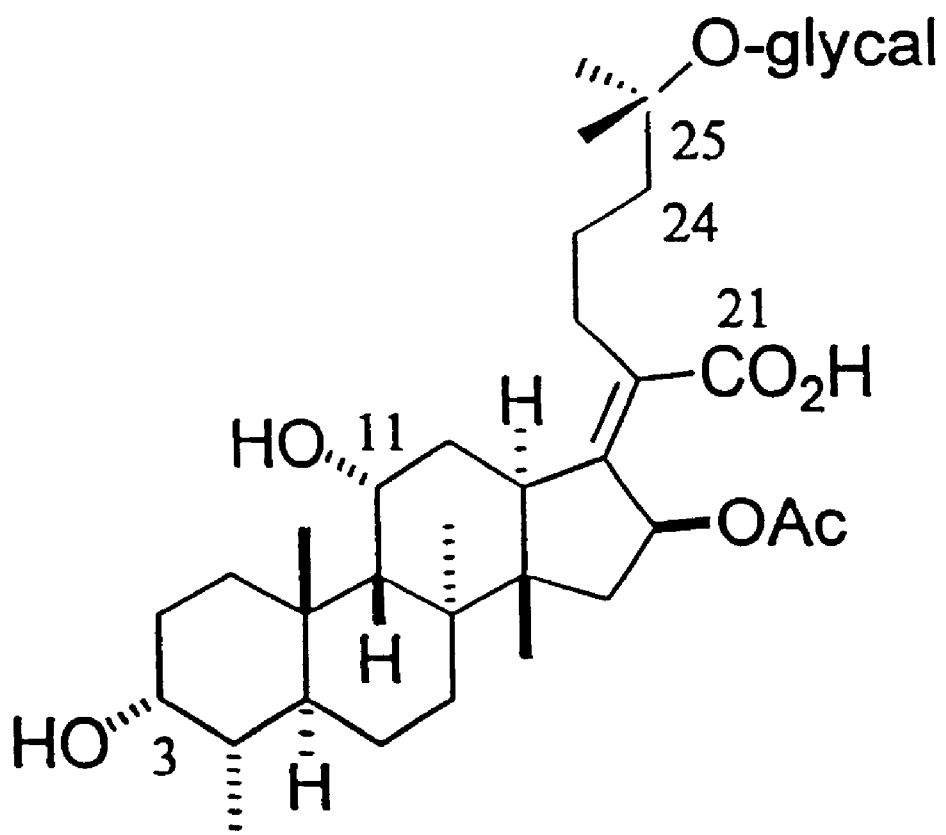
FIG. 27 shows the structure of a fusidic acid analog contemplated by the present invention that has a carbohydrate unit at position C-25.

The molecule in FIG. 24 will be glycosylated by following the standard procedure described in Examples 23 and 25 which employs the permonochloroacetylated glycals. Thus, a number of glycosylated fusidic acid derivatives such as that depicted in FIG. 26 will be prepared where the carbohydrate attached at the C-25 hydroxyl will be, for example, the permonochloroacetylated glucal, maltal, or lactal. The protecting groups of the glycosylated derivative can be hydrolyzed by following the procedure outlined in Experimentals 24 and 14 to hydrolyze the monochloroacetyls and methyl ester, respectively. These reactions will give the molecule shown in FIG. 27.

Figure 25:
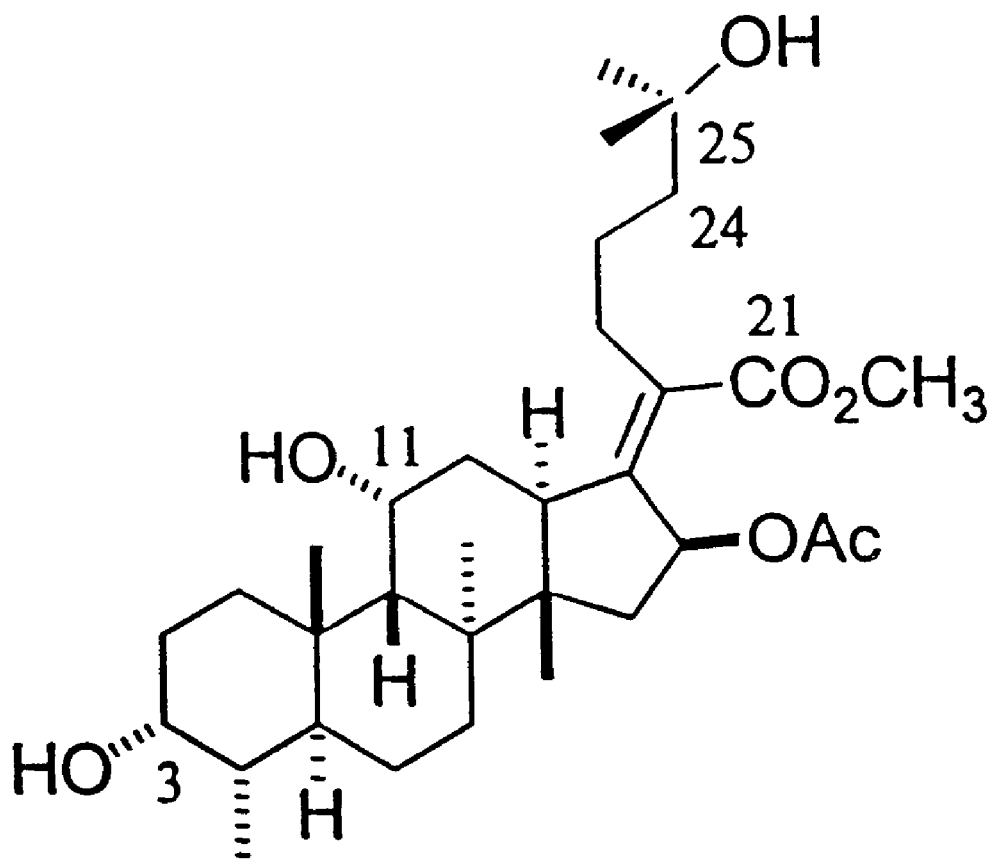
FIG. 25 shows the structure of a fusidic acid analog contemplated by the present invention that has a protecting group at position C-21 and an hydroxyl group at position C-25.
Figure 28:
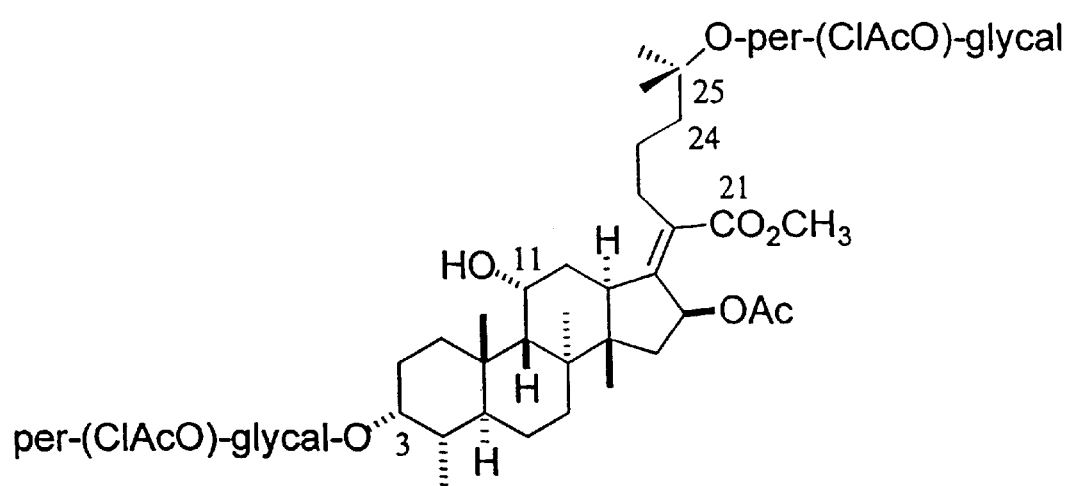
FIG. 28 shows the structure of a fusidic acid analog contemplated by the present invention that has a protecting group at position C-21 and at each of positions C-3 and C-25 a carbohydrate unit having protecting groups.
Figure 29:
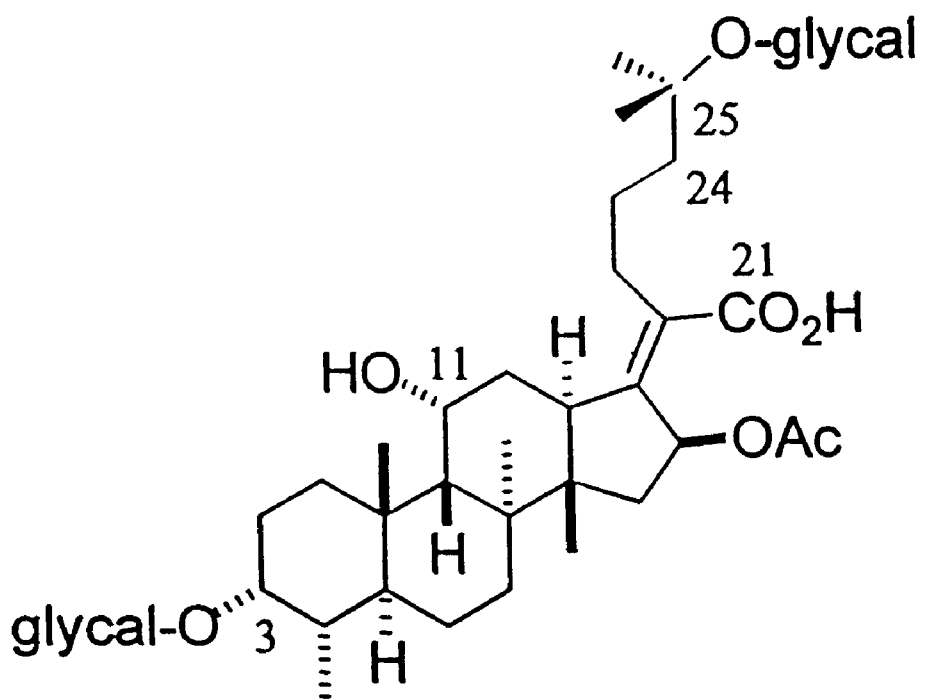
FIG. 29 shows the structure of a fusidic acid analog contemplated by the present invention that has a carbohydrate unit at each of positions C-3 and C-25.

Alternatively, the modified fusidic acid of FIG. 24 can first be deprotected by following the protocol in Experimental 24 to give the modified fusidic acid in FIG. 25 which has no protected hydroxyl groups yet still has a protected carboxylic acid at C-21. Reaction of this compound with 2.1 equivalents of a permonochloroacetylated glycal according to the protocol in Experimentals 23 and 25 will give the twice glycosylated analog of fusidic acid as shown in FIG. 28. The protecting groups can then be removed as discussed above by following Experimentals 24 and 14 to give the molecule depicted in FIG. 29.

What is claimed is:

1. A composition comprising an O-glycoside analog of fusidic acid, wherein said fusidic acid has an acetate group at the C-16 position, a carboxylic acid at the C-21 position, and a cyclic carbohydrate attached via an oxygen atom at one or more positions selected from the group consisting of the C-3 position, the C-24 position, and the C-25 position.

2. The composition of claim 1, wherein said carbohydrate is selected from the group consisting of a monosaccharide and disaccharide.

3. The composition of claim 2, wherein said O-glycoside analog is fusidic acid 3-(4,6-di-O-acetyl-2,3-dideoxy-α-D-erythro-hex-2-enopyranoside).

4. The composition of claim 2, wherein said O-glycoside analog is fusidic acid 3-(2,3-dideoxy-α-D-erythro-hex-2-enopyranoside).

5. The composition of claim 2, wherein said O-glycoside analog is 11-dehydrofusidic acid 3-(4,6-di-O-acetyl-2,3-dideoxy-c*-D-erythro-hex-2-enopyranoside).

6. The composition of claim 2, wherein said O-glycoside analog is 11-dehydrofusidic acid 3-(2,3-dideoxy-α-D-erythro-hex-2-enopyranoside).

7. The composition of claim 2, wherein said O-glycoside analog is 24,25-dihydrofusidic acid 3-(4,6-di-O-acetyl-2,3-dideoxy-α-D-erythro-hexanopyranoside).

8. The composition of claim 2, wherein said O-glycoside analog is 24,25-dihydrofusidic acid 3-(2,3-dideoxy-α-D-erythro-hexanopyranoside).

9. The composition of claim 2, wherein said O-glycoside analog is 11-dehydro-24,25-dihydrofusidic acid 3-(4,6-di-O-acetyl-2,3-dideoxy-α-D-erythro-hexanopyranoside).

10. The composition of claim 2, wherein said O-glycoside analog is 11-dehydro-24,25-dihydrofusidic acid 3-(2,3-dideoxy-α-D-erythro-hexanopyranoside).

11. The composition of claim 2, wherein said O-glycoside analog is fusidic acid 3-[4-O-(2,3,4,6-tetra-O-acetyl-α-D-glucopyranosyl)-6-O-acetyl-2,3-dideoxy-α-D-erythro-hex-2-enopyranoside].

12. The composition of claim 2, wherein said O-glycoside analog is fusidic acid 3-[4-O-(2,3,4,6-tetra-O-acetyl-β-D-galactopyranosyl)-6-O-acetyl-2,3-dideoxy-α-D-erythro-hex-2-enopyranoside].

13. The composition of claim 2, wherein said O-glycoside analog is fusidic acid 3-(4,6-bis-O-(chloroacetyl)-2,3-dideoxy-α-D-erythro-hex-2-enopyranoside.

14. The composition of claim 2, wherein said O-glycoside analog is fusidic acid 3-[4-O-(2,3,4,6-tetra-O-(chloroacetyl)-α-D-glucopyranosyl)-6-O-(chloroacetyl)-2,3-dideoxy-α-D-erythro-hex-2-enopyranoside].

15. The composition of claim 2, wherein said O-glycoside analog is fusidic acid 3-[4-O-(2,3,4,6-tetra-O-(chloroacetyl)-β-D-galactopyranosyl)-6-O-(chloroacetyl)-2,3-dideoxy-α-D-erythro-hex-2-enopyranoside].

16. The composition of claim 2, wherein said O-glycoside analog is fusidic acid 3-[4-O-(α-D-glucopyranosyl)-2,3-dideoxy-α-D-erythro-hex-2-enopyranoside].

17. The composition of claim 2, wherein said O-glycoside analog is fusidic acid 3-[4-O-(β-D-galactopyranosyl)-2,3-dideoxy-α-D-erythro-hex-2-enopyranoside].

18. The composition of claim 2, further comprising a diluent selected from the group consisting of water, saline, dextrose, glycerol, ethylene glycol and propylene glycol.

19. A composition comprising a modified form of fusidic acid, wherein said fusidic acid has an acetate group at the C-16 position, and a protecting group at the C-11 position.

20. The composition of claim 19, wherein said protecting group is selected from the group consisting of acetate, monochloroacetyl, methoxyacetal and methyl.

21. A composition comprising a modified form of fusidic acid, wherein said fusidic acid has an acetate group at the C-16 position, and a protecting group at one or more positions selected from the group consisting of the C-3 position, the C-11 position, and the C-21 position, and further comprising a cyclic carbohydrate at one or more positions selected from the group consisting of the C-3 position, the C-24 position, and the C-25 position.

22. The composition of claim 21, wherein said carbohydrate is selected from the group consisting of a monosaccharide and disaccharide.

23. The composition of claim 22, further comprising a diluent selected from the group consisting of water, saline, dextrose, glycerol, ethylene glycol and propylene glycol.

* * * * *